United States Patent [19]

Pless et al.

[11] Patent Number: 5,111,816
[45] Date of Patent: May 12, 1992

[54] SYSTEM CONFIGURATION FOR COMBINED DEFIBRILLATOR/PACEMAKER

[75] Inventors: Benjamin Pless, Menlo Park; John G. Ryan; James M. Culp, both of San Jose, all of Calif.

[73] Assignee: Ventritex, Sunnyvale, Calif.

[21] Appl. No.: 600,257

[22] Filed: Oct. 22, 1990

Related U.S. Application Data

[63] Continuation of Ser. No. 355,927, May 23, 1989, abandoned.

[51] Int. Cl.⁵ ............................................. A61N 1/362
[52] U.S. Cl. ........................... 128/419 PG; 128/419 D
[58] Field of Search ...................... 128/419 D, 419 PG

[56] References Cited

U.S. PATENT DOCUMENTS

| | | | |
|---|---|---|---|
| 4,285,345 | 8/1981 | Mensink et al. | 128/419 PG |
| 4,337,776 | 7/1982 | Daly et al. | 128/419 PT |
| 4,552,150 | 11/1985 | Zacouto | 128/419 PG |
| 4,787,389 | 11/1988 | Tarjan | 128/419 D |
| 4,800,883 | 1/1989 | Winstrom | 128/419 D |
| 4,830,006 | 5/1989 | Haluska et al. | 128/419 PG |

OTHER PUBLICATIONS

Winkle et al., "Improved Low Energy Defibrillation Efficacy in Man with the Use of a Biphasic Truncated Exponential Waveform", American Heart Journal, (Jan. 1989), pp. 122–127.

Goodenough, Frank, "MOS-Controlled Thyristor Turn Off 1MW in 2 μS", Electronic Design, Nov. 10, 1989, pp. 57–60.

Schuder et al., "Is the Effectiveness of Cardiac Ventricular Defibrillation Dependent Upon Polarity?", Medical Instrumentation, vol. 21, No. 5, (1987) pp. 262–265.

Primary Examiner—William E. Kamm
Assistant Examiner—Scott M. Getzow
Attorney, Agent, or Firm—Limbach & Limbach

[57] ABSTRACT

The present invention is directed to various features of an implantable combined defibrillation/pacemaker system. The system's defibrillation delivery circuit provides for delivery of a multi-phase defibrillation waveform. It also includes features for insuring low patient current leakage. Protection circuitry is provided for protecting the pacing circuitry from damage by the high voltage defibrillation output. The dual channel cardiac pacing circuit accommodates bipolar and pseudo-unipolar pacing. The system includes the ability to detect defibrillator lead breaks without delivering a defibrillation pulse to the patient. An additional advantage of the disclosed system is its ability to use the pacing output stage for extremely high rate pacing to induce ventricular fibrillation.

37 Claims, 14 Drawing Sheets

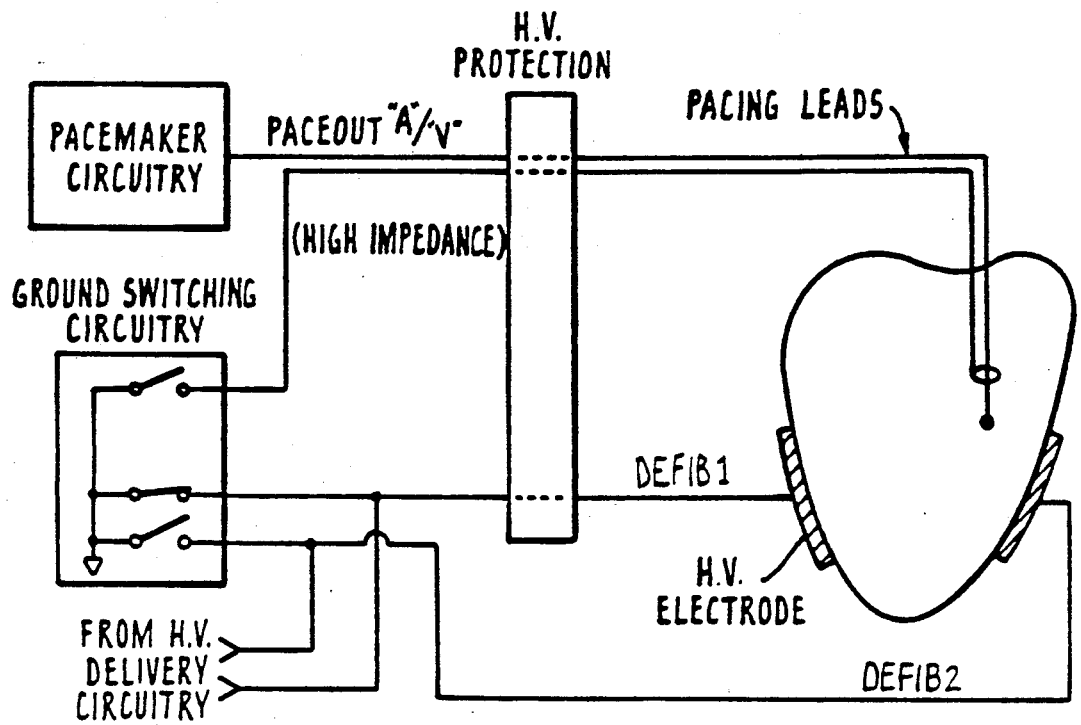
FIG. 16A.
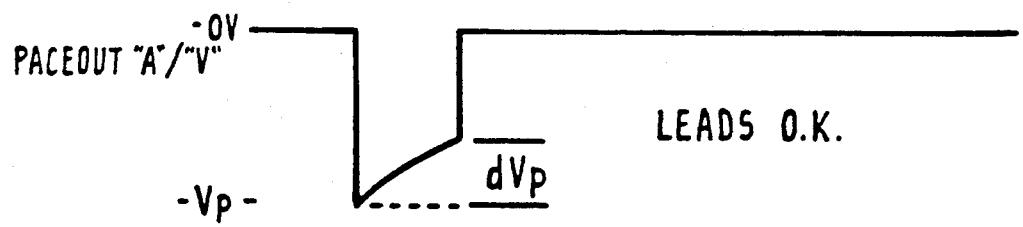
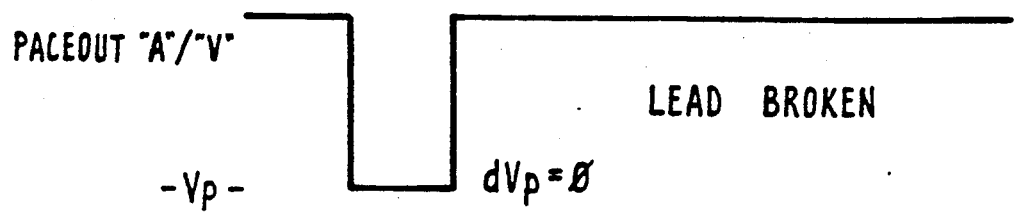
FIG. 16B.

SYSTEM CONFIGURATION FOR COMBINED DEFIBRILLATOR/PACEMAKER

This is a continuation of co-pending application Ser. No. 355,927 filed on May 23, 1989, now abandoned.

FIELD OF THE INVENTION

The present invention relates to implantable medical devices and, in particular, to features of an implantable combined defibrillator/pacemaker.

BACKGROUND OF THE INVENTION

In recent years, there has been a great deal of interest in the application of very low power analog/digital circuitry in battery powered biomedical systems. Much of this interest has centered around implantable cardiac pacemakers. These devices are used to treat cardiac arrhythmias, such as bradycardia (slow heart rate) or tachycardia (rapid heart rate), by assisting the heart's natural pacemaking function with relatively low voltage (5-10 V) pulses.

This type of treatment is, however, totally ineffective against fibrillation, which is characterized by very rapid, uncoordinated electrical activity in which the heart essentially stops pumping blood. Death quickly results unless emergency treatment, generally in the form of a defibrillating high voltage shock, is administered. It is estimated that each year in the U.S. about 300,000 people suffer sudden death from this condition.

As the technology for defibrillators improves, it becomes possible to more completely combine both pacing and defibrillation capabilities in a single implantable device. This results in significant performance improvements.

It is well recognized that biphasic defibrillation is more effective than monophasic defibrillation. Winkle et al., "Improved low energy defibrillation efficacy in man with the use of a biphasic truncated exponential waveform", American Heart Journal, January 1989, pp. 122-127.

U.S. Pat. No. 4,800,883 issued Jan. 31, 1989, to William L. Winstrom, discloses an apparatus for generating a multiphasic defibrillation waveform. The Winstrom apparatus is suitable for use in an implantable defibrillation system for automatically generating a multiphasic defibrillation pulse waveform in response to sensed fibrillation. A controller senses cardiac fibrillation and generates a control signal that causes a charging circuit to charge two series charge-storing capacitors to selected voltage levels in sequentially alternating charge generation and charge coupling cycles. A voltage level detector senses the stored voltage level, disables the charging circuit when the sensed voltage reaches a predetermined level and informs the controller that the capacitors are fully charged. The controller then communicates control signals indicative of pulse magnitude, duration and polarity to a multiphasic pulse generator that includes a number of high-power switches and corresponding switch drivers interposed in-circuit between the heart and the terminals of the charge storing capacitors. The drivers control the conduction states of the switches according to the control signals to establish selected circuit paths between the capacitor terminals and the heart, thereby delivering to the heart a multiphasic waveform having pulses with selected parameters of magnitude, duration and polarity.

SUMMARY OF THE INVENTION

The present invention provides an implantable system that includes both a pacemaker and a fully programmable defibrillator and, thus, may be used in the treatment of bradycardia and tachycardia as well as ventricular fibrillation.

The system design uses a minimum number of components, which enhances reliability, and includes safety features that reduce the leakage current to the patient.

Whether the defibrillation output stage is monophasic or biphasic, it is desirable to non-invasively ascertain whether a break has occurred in the defibrillating leads without having to subject the patient to a traumatic high voltage defibrillating pulse. Special features are included in the pacing output section of the system for this purpose.

An additional requirement for a combined pacemaker/defibrillator device is that the pacing circuit be able to deliver pacing pulses at an extremely high rate (50 per second) without droop to fibrillate the patient intentionally. This gives the physician the ability to non-invasively induce the patient's arrhythmia and thereby verify proper functionality of the automatic features of the device.

In conventional implantable defibrillators, large positive voltages are produced and pulsed into the heart to terminate ventricular arrhythmias. These large voltages would have the effect of destroying the low voltage pacing circuitry which is also connected to the cardiac tissue if high voltage protection were not present. Protection from such high voltages, without shunting current, requires a device which in the off state can stand-off these voltages. Also, when "on", a protection device requires a low "on" resistance so as not to significantly increase the source impedance of the pacing circuitry. Ideally, this low "on" resistance must also be achievable with a controlling voltage no greater than the battery voltage. High voltage MOSFET devices which have the required characteristics are available at present. In general, only n-channel devices have the required voltage standoff of about 1 kV. This precludes the use of a battery in a negative power supply configuration. Thus, a voltage inverter is required to generate pacing pulses.

Accordingly, the present invention provides a combined defibrillator/pacemaker system whereby the pacing voltage and the defibrillation voltage are both regulated as positive voltages above ground. The system power supply is also a positive voltage above ground. Both phases of the defibrillation pulse are delivered as a positive voltage relative to ground, making protection of the pacing output simple. Pacing is delivered as a negative capacitor-coupled voltage for patient safety. The defibrillator output stage forms an H pattern of high voltage/high current switches allowing the load, i.e. the heart, polarity to be reversed. Depending on the phasing of the switches, monophasic or biphasic pulses of either initial polarity can be generated. In a preferred embodiment, MOS controlled thyristors are utilized to implement switching. Leakage current shunt resistors are strategically placed to reduce the possibility of direct current leakage to the patient while the switches are standing off high voltage. Snubber diodes in parallel with the shunt resistors protect the output stage from voltage spikes when switching inductive loads. The floating transistor on each of the ground stages has a protection circuit that keeps gate voltage spikes from turning on the stage inappropriately during defibrillation. If the stage were to inappropriately turn on, it would result in the destruction of the output. The oscillator which energizes the gate drive magnetics is configured to keep the peak magnetic fields relatively constant over the range of battery voltages experienced from beginning of battery life to end of service.

The use of defibrillation pulses that are positive with respect to ground allows the protection of the pacing output stage to be reduced to its simplest configuration. High voltage n-channel MOSFETs are placed in series with each of the active pacing leads and the pacing ground return leads. The gates of these devices are controlled by a signal which is normally at battery voltage, turning the MOSFETs on and allowing pacing to occur normally. Just prior to generating the defibrillation output and for a brief time thereafter, the gates of the MOSFETs are held low, turning them off and thereby protecting the pacing output stage.

A dual channel, i.e. atrial and ventricular, pacing pulse delivery circuit delivers, in programmable fashion, pulsatile voltages up to and including twice the open circuit battery voltage. The polarity of these pulses is negative with respect to ground, the battery voltage being positive. The configuration of switches that delivers the pacing pulses to the patient can also be used in a single channel pace pulse delivery circuit.

An alternate switch configuration provides a single channel pace pulse delivery circuit. The difference between this configuration and that referred to above is that it cannot standoff an external negative transient, i.e. from the other pace channel. The pacing ground return lead is switchable between one of the dedicated pacing return leads and one of the defibrillation electrodes to allow programmability between conventional bipolar pacing and a pseudo-unipolar pacing. The pseudo-unipolar pacing configuration can also be used with a minimal lead system configuration whereby the EKG sensing is also pseudo-unipolar rather than the conventional differential sensing.

By using a standard pacing impedance measuring scheme and allowing each of the patches to be switched to ground independently so the system can pace in a quasi-unipolar fashion with respect to either of the high voltage electrodes, the lead integrity of the defibrillation leads can be ascertained. Furthermore, the measurements can occur automatically and at regular intervals to provide an early warning of a defibrillation lead failure.

In summary, an implantable combined defibrillator-pacemaker system in accordance with the present invention provides a number of advantageous features not found in systems of the type taught by the '883 Winstrom patent. A biphasic waveform delivery circuit that utilizes MOS Controlled Thyristors (MCT) is disclosed. These devices are ideal for this application in that they can switch much higher currents than either IGFETs or MOSFETs. A biphasic waveform delivery circuit that utilizes eight IGFETs which can switch in excess of 800 V on both phases of the delivered waveform is disclosed; the type of high voltage switches and circuit disclosed by Winstrom limit the HV to substantially below this voltage. A biphasic waveform delivery circuit that utilizes six IGFETs is disclosed. This circuit limits the second phase voltage to a maximum of one-half the first phase voltage. A circuit technique which maintains magnetic field strength in the tranformers of the 8-IGFET and 6-IGFET delivery circuits approximately constant with respect to battery voltage is disclosed; this allows for more optimal magnetics design. To enhance patient safety, methods of reducing leakage currents to the patient utilizing a minimum number of components are disclosed. The use of snubber diodes to enhance the reliability of the biphasic waveform delivery circuits is disclosed. Methods of detecting defibrillation lead breakage without the necessity of delivering a high voltage shock to the patient are disclosed.

Other features and advantages of the present invention will be appreciated by reference to the detailed description of the invention provided below, which should be considered in conjunction with the accompanying drawings.

BRIEF DESCRIPTION OF THE DRAWINGS

FIGS. 16A and 16B are a simplified schematic diagram and timing diagram, respectively, illustrating the detection of defibrillation lead breakage in accordance with the present invention.

DETAILED DESCRIPTION OF THE INVENTION

Figure 1:
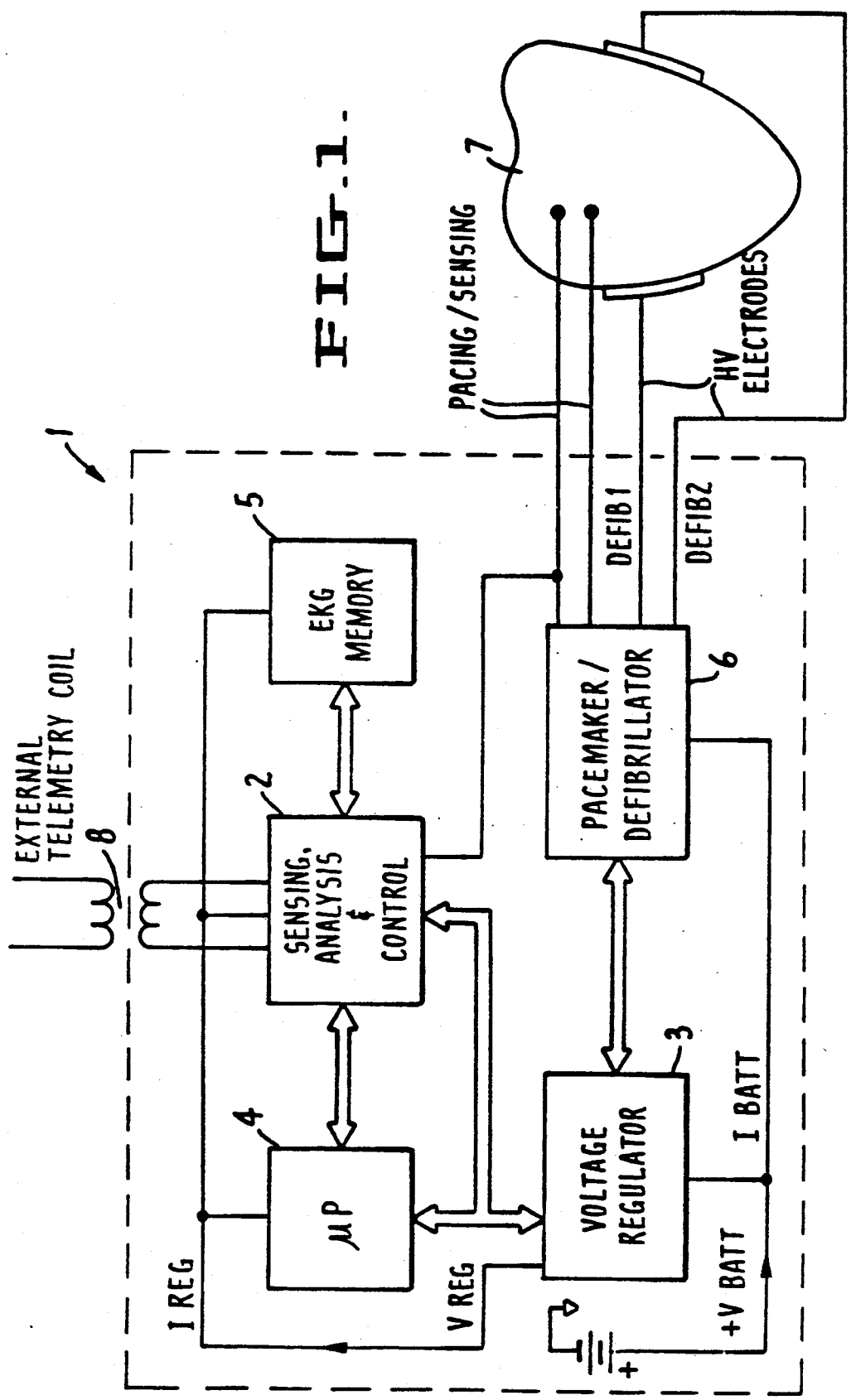
FIG. 1 is a block diagram illustrating the general organization of an implantable combined defibrillator/pacemaker system.

FIG. 1 provides a block diagram showing the general organization of an implantable combined defibrillator/pacemaker system 1. The system 1 includes sensing, analysis and control circuitry 2, a voltage regulator circuit 3 and an 8-bit microprocessor 4. A static RAM 5 is used to store digitized EKG waveforms. External connections from pacemaker/defibrillator circuitry 6 to the heart 7 are provided by two high voltage electrodes DEFIB1 and DEFIB2 and pacing/sensing leads through which millivolt level EKG signals are sensed and which also carry pace pulses to the heart 7. Telemetry to and from an external programmer is carried via a coil-to-coil link 8. System software decides whether the EKG parameters indicate an arrythmia and, if so, the appropriate therapy is initiated. The raw EKG data can also be stored in memory 5 for later retrieval or be telemetered out of the system 1 in real time.

Figure 2:
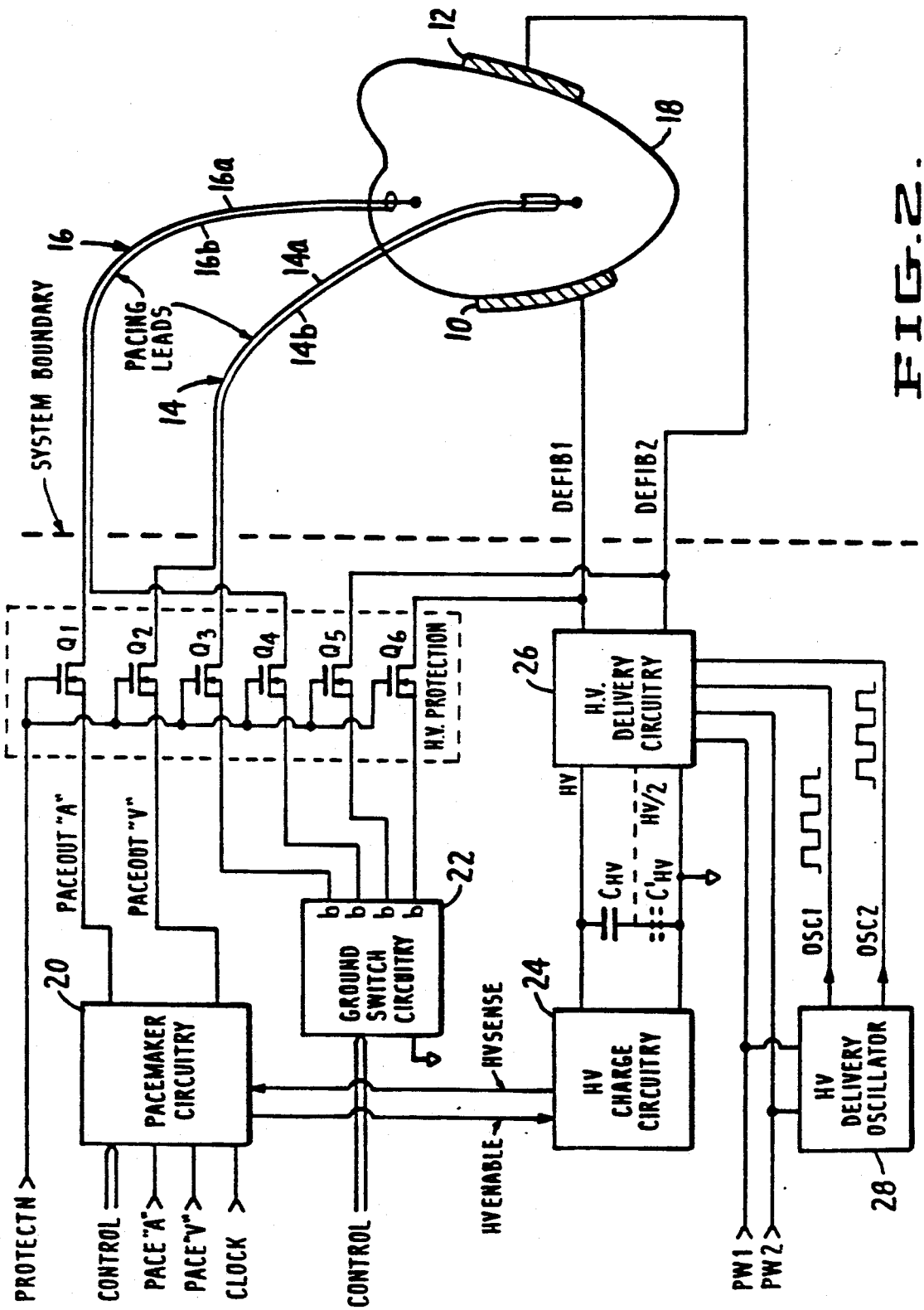
FIG. 2 is a block diagram illustrating an embodiment of a combined defibrillator/pacemaker system in accordance with the present invention.

FIG. 2 shows a block diagram embodiment of defibrillator/pacemaker circuit 6 in accordance with the present invention with its full complement of cardiac leads. These leads comprise two high voltage defibrillation electrodes 10 and 12 and two sets 14 and 16 of pacing leads. The heart 18 is defibrillated by high voltage pulses which are delivered through leads DEFIB1 and DEFIB2 to electrodes 10 and 12, respectively.

The two sets 14,16 of pacing leads, each set comprising an active lead (14a,16a) and a ground return (14b,16b), are connected to pacemaker circuitry 20 and to ground switch circuitry 22, respectively, via high voltage protection MOSFETS Q1-Q4. The high voltage leads DEFIB1 and DEFIB2 are also connected to the ground switch circuitry 22 via protection MOSFETS Q5 and Q6, respectively. The function of MOSFETS Q1-Q6 will be described in greater detail below.

HV charge circuitry 24 charges a high voltage capacitor $C_{HV}$ or capacitor stack to a regulated voltage of up to 1 kV. More than one capacitor may be needed to stand off the required voltage; a second capacitor $C'_{HV}$, illustrated in FIG. 1 in dotted lines, is representative of a capacitor stack. One of the embodiments of high voltage delivery circuit 26 discussed in greater detail below uses the center tap HV/2 of these two capacitors to allow for a reduced charging configuration.

HV delivery circuitry 26 is controlled by logic lines PW1 and PW2, as described below. HV delivery oscillator 28 provides timing signals OSC1 and OSC2 to HV delivery circuitry 26 in those embodiments that utilize IGFET delivery circuits; this is also discussed in greater detail below.

Figure 3:
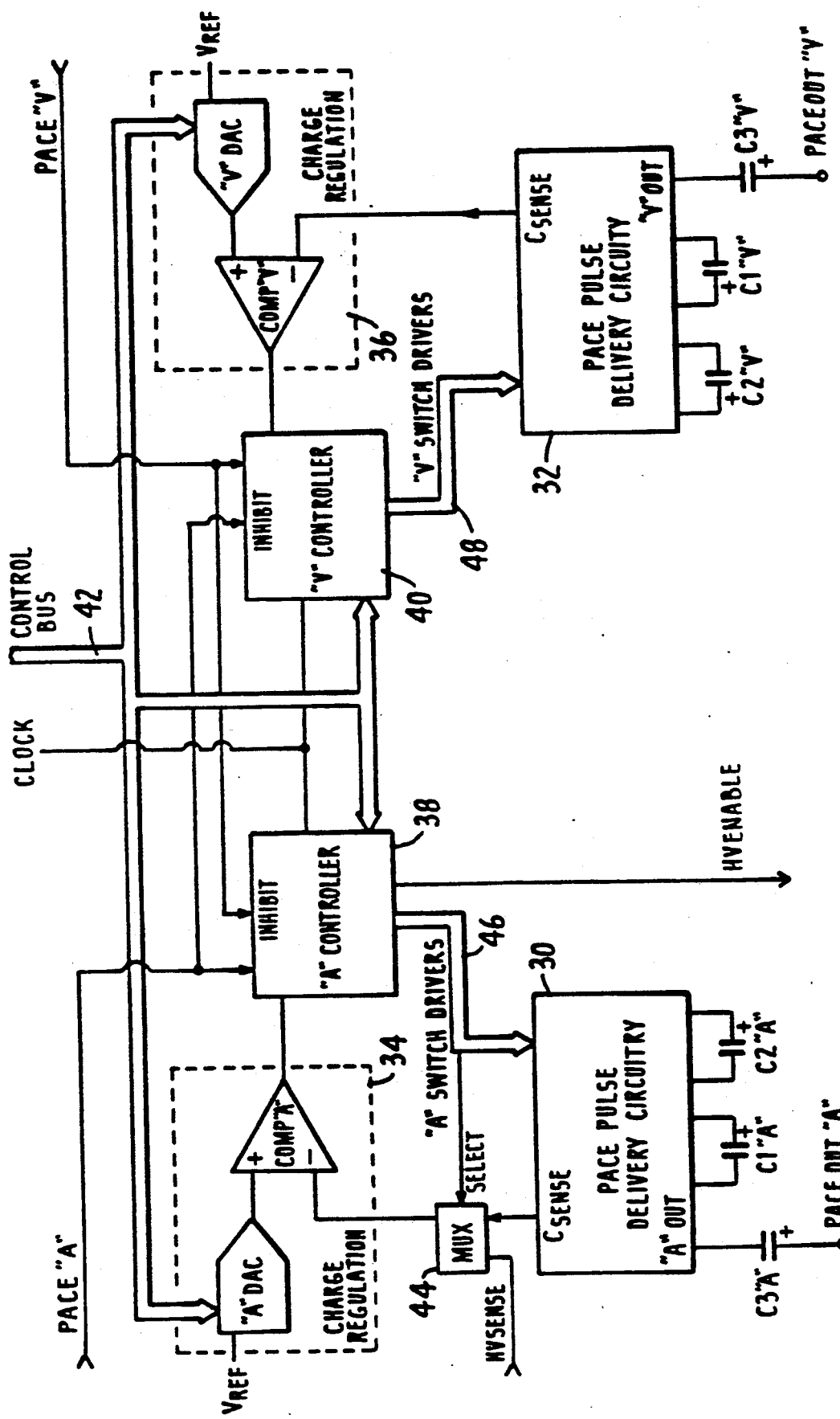
FIG. 3 is a block diagram illustrating an embodiment of pacemaker circuitry that can be utilized in the FIG. 2 system.

FIG. 3 shows an embodiment of the pacemaker circuitry 20. The pacemaker circuitry 20 includes two substantially identical pacing channels "A" and "V", each including a pace pulse delivery circuit (30,32), charge regulation circuit (34,36), controller circuit (38,40), and pace pulse generation and delivery capacitors C1, C2, C3.

"A" and "V" channel pacing pulses are produced in response to assertion of control lines PACE"A" or PACE"V", respectively, by the system microprocessor 4 and associated sensing, analysis and control circuitry 2.

Similarly, the control bus 42 allows the pacing voltage amplitude to be programmed via the "A"/"V" DAC's which form part of the charge regulation circuit (34 and 36). This control bus 42 also allows the pacing mode to be programmed, i.e. whether the voltage amplitude is to be doubled by connecting capacitors C1 and C2 in series during pace delivery, or whether the capacitors are to be discharged between pace deliveries, or whether the charge regulation circuitry (34 and 36) is to be ignored during capacitor charging to allow charging to the open circuit battery voltage and, hence, achieve the maximum output pulse amplitude possible.

In the described embodiment, the atrial or "A" channel charge regulation circuit 34 and controller circuit 38 can also be used to regulate the voltage to which the HV charge circuit 24 charges the capacitor stack for delivery of defibrillation pulses. Note in FIG. 3 the addition of a multiplexor 44 which muxes both the pacing capacitor voltage and the HVSENSE line to the regulation circuitry 34.

The voltage on the HVSENSE line tracks HV using a resistive divider to scale into the active range of the regulation circuitry 34.

Conventional bipolar pacing takes place between the pacing outputs (PACEOUT"A"/"V") delivered to the heart by the active leads (14a,16a) and the switched ground return leads (14b,16b) (tip to ring). Pseudo-unipolar pacing takes place between the active pacing leads (14a,16a) and one of the high voltage defibrillation electrodes (10,12). In either case, the loading effect of the cardiac impedance can be modelled as a resistor with a nominal value of 500 ohms.

Figure 4:
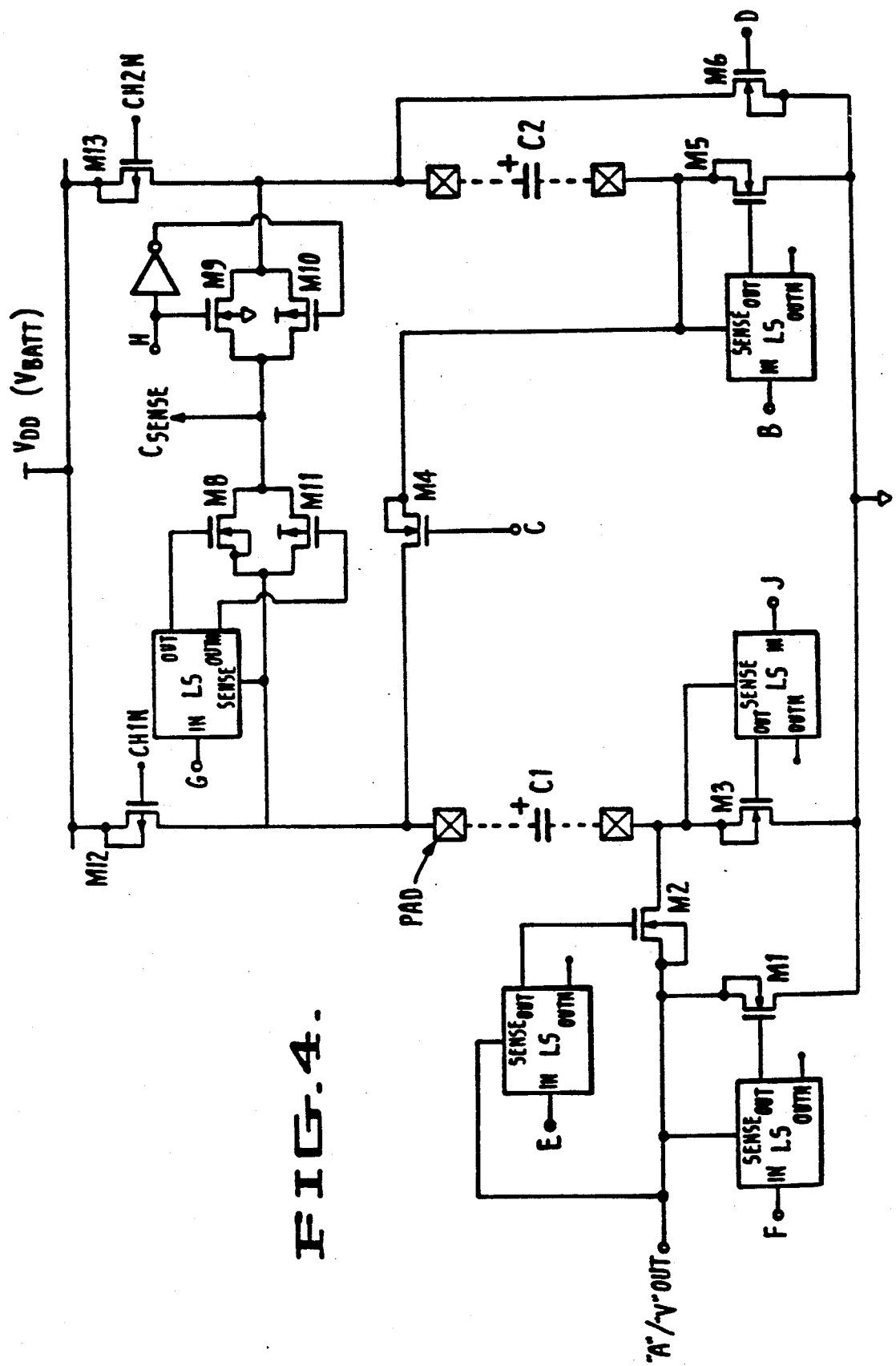
FIG. 4 is a schematic diagram illustrating an embodiment of pace pulse delivery circuitry that can be utilized in the FIG. 2 system.

FIG. 4 shows a configuration of n-channel and p-channel MOS switches which comprise the pace pulse delivery circuit 30,32 used in the "A" and "V" channels, respectively. The circuit blocks marked "LS" in FIG. 4 are level shifters which shift the gate drive voltages to the n-channel switches negatively to track the negative going pace pulse. This is necessary to keep the appropriate switches off during pace delivery.

Capacitors C1 and C2 in FIG. 4 are the capacitors shown in FIG. 3 as C1"A"/"V" and C2"A"/"V", respectively. These are discrete capacitors which have values in the 10-30 microfarad range.

As further shown in FIG. 4, the switches of the pace pulse delivery circuit (30,32) are controlled by lines B through J, CH1N and CH2N. In FIG. 3, these control lines are shown as a bus marked "A"/"V" SWITCH DRIVERS (46,48).

Figure 5:
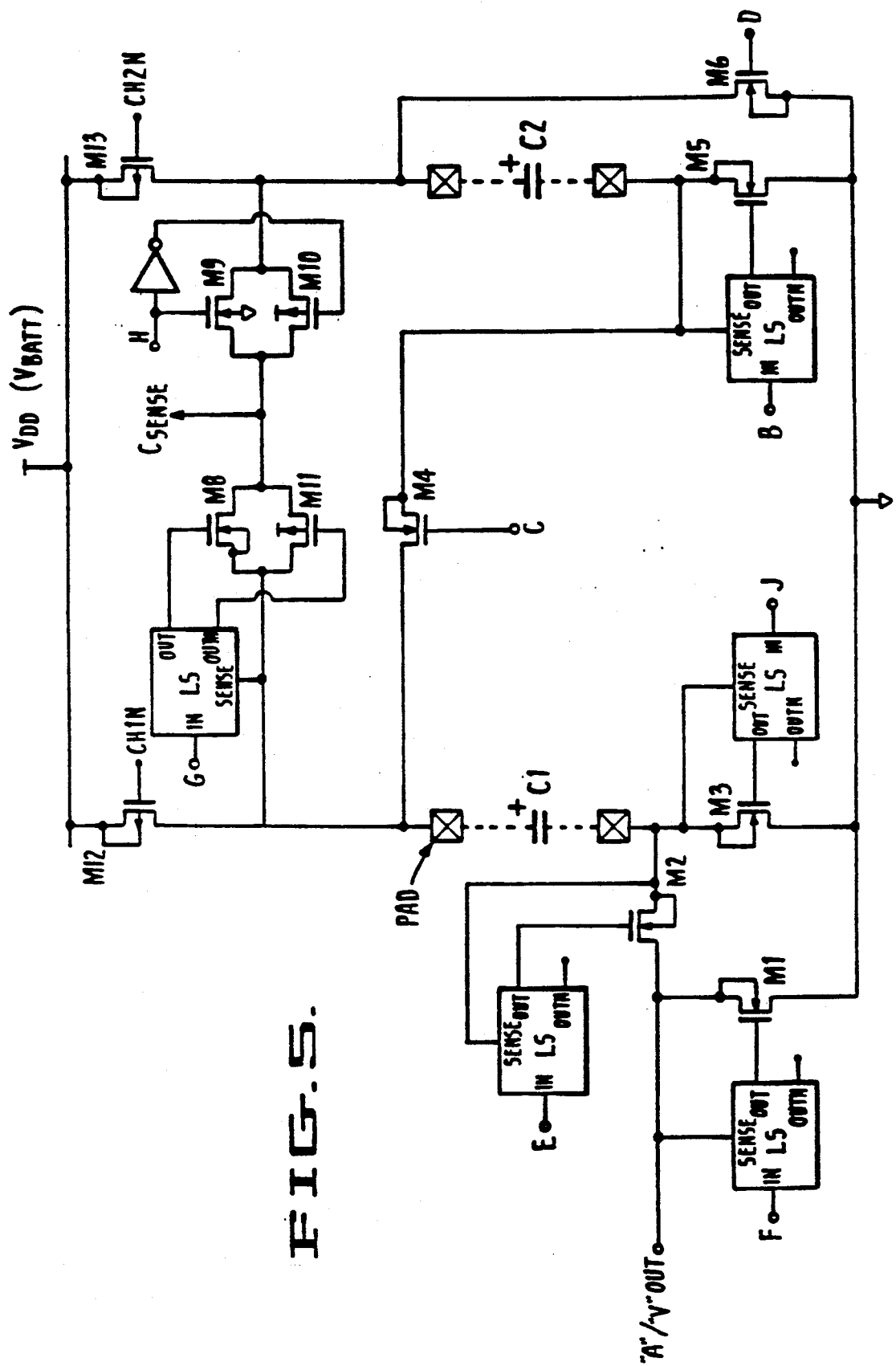
FIG. 5 is a schematic diagram illustrating an embodiment of pace pulse delivery circuitry that can be utilized in a single channel configuration of the FIG. 2 system.

FIG. 5 shows an alternate pace pulse delivery circuit (30,32) which can be used only in the single channel case.

Figure 8:
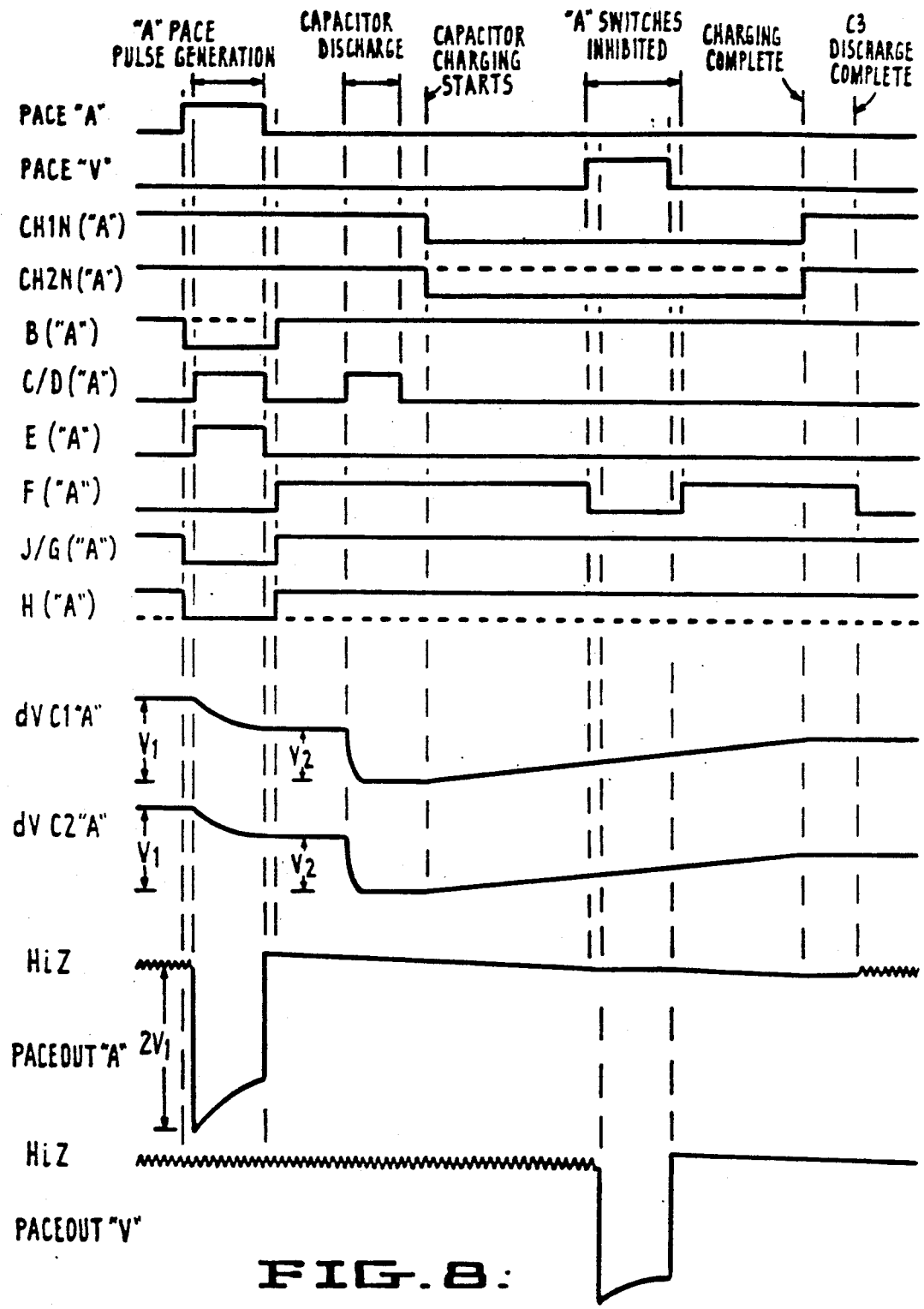
FIG. 8 is a timing diagram illustrating switch drive and capacitive charging waveforms associated with a typical "A" channel pace cycle of the system shown in FIG. 2, including the interaction of a "V" channel pace cycle.

Referring to FIGS. 2 and 8, the output PACEOUT"A" and PACEOUT"V" of channels "A" and "V", respectively, of the pacemaker circuitry 20 is a negative going pulse the width of which is controlled by the corresponding control line PACE"A"/"V" and the amplitude of which is a function of the capacitor voltages (C1,C2 in FIG. 3) and the mode in which the capacitors are stacked to provide the output. The total resistive impedance of the pacemaker circuitry 20, ground switching circuitry 22 and HV protection circuitry (devices Q1-Q6) should be a small percentage of the cardiac load impedance which, as stated above, is in the 500 ohm range. Hence, assuming 5% losses, the total impedance of these circuits cannot exceed 25 ohms.

Capacitors C3 "A"/"V" are not strictly necessary for circuit operation, but are included to fulfill a regulatory obligation that there not be a DC current path between the pacing electronics and the patient. Capacitor C3, however, also reduces the source capacitance of the pace pulses.

Referring to the pace pulse delivery circuitry (30, 32) shown in FIGS. 4 and 5, in each embodiment, the pace pulse delivery function is carried out by n-channel transistors M1 through M6. Switches M2 through M6 are designed to be very low impedance, since they either deliver the output pulse or carry charging current. A typical impedance value for these devices is 5 ohms.

Consider the case where capacitors C1 and C2 are initially charged to a voltage $+V1$, the top plates being at this positive potential and the bottom plates being connected to ground through switches M3 and M5, respectively. In this case, switches M1, M2, M4, and M6 are off and switches M3 and M5 are on. At this point, the output node "A"/"V"OUT is isolated. This is illustrated in FIG. 8 as a noisy trace on PACEOUT'-'A"/"V".

To generate a pace pulse, first switches M3 and M5 are switched off. If an output voltage equal to $-2V1$ is required, then switches M2, M4 and M6 are turned on simultaneously. The positive plate of capacitor C2 is thus connected to ground, thereby pumping its bottom plate to $-V1$. The bottom plate of capacitor C2 is connected via switch M4 to the positive plate of capacitor C1, thereby pumping the bottom plate of capacitor C1 to $-2V1$. This voltage is connected to the output node via switch M2. Note the configuration of the bulk connections of switches M1 through M6 to allow for operation below the negative power supply rail. It will be clear to those skilled in the art that this type of bulk connection implies the use of a P-well or twin tub CMOS process if integration of these devices is required.

The bulk connection of transistor M2 of FIGS. 4 and 5 should be inspected closely. In the dual channel case, i.e. the FIG. 4 embodiment, the bulk of transistor M2 and the "SENSE" inputs to the appropriate level shifter LS are connected to the output node "A"/"V"OUT. This results in a negative voltage appearing on the output node, i.e a pace pulse from the other pacing channel is blocked by transistor M2. In the single channel only case, i.e. the FIG. 5 embodiment, the bulk of transistor M2 is connected towards the negative plate of capacitor C1. Thus, a negative voltage on the output node is not blocked by transistor M2 and, hence, this circuit cannot be used in a dual channel pace pulse generator.

The advantage of the FIG. 5 single channel only configuration is the manner in which transistor M2 is biased during a pace pulse delivery. In this configuration, the bulk of transistor M2 is always guaranteed to be more negative than the output node, i.e. the drain of transistor M2. Hence, the intrinsic drain p-n junction is always reverse biased. Thus, to a first order, there is no limit to the current that may be delivered through transistor M2. Hence, delivering a pulse into a short circuit presents no difficulty.

In the dual channel case shown in FIG. 4, the drain of transistor M2, i.e. the end connected to capacitor C1, swings more negative than the bulk by a voltage equal to the product of the delivered current and the switch impedance. Hence, there is a possibility of forward biasing the drain p-n junction during pace pulse delivery. In general, because transistor M2 is on during pace pulse delivery, a forward biased drain diode should have no effect. However, at very high current levels, this configuration should be used with care due to the possibility of forward biasing the p-n junction.

As the source and, thereby, bulk connections of transistors M1 through M6 swing negatively, it is clear that to preserve the "off" condition of devices M1, M3 and M5, the gate drive of each of these devices must track its source voltage; hence, the use of level shifters LS.

Figure 6:
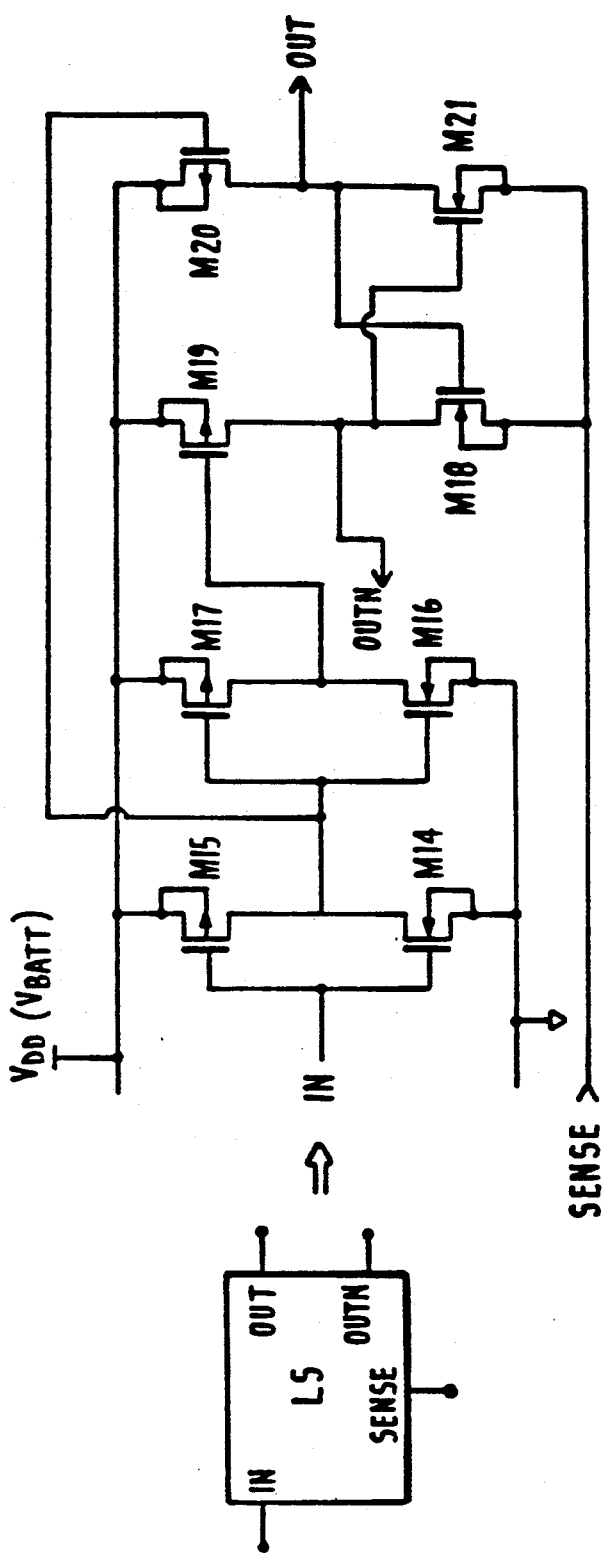
FIG. 6 is a schematic diagram illustrating an embodiment of level shifting circuitry that can be utilized in the pace pulse delivery circuitry shown in FIGS. 4 and 5.

An embodiment of the type of level shifter used in the FIG. 4 and 5 circuits is shown in FIG. 6. It will be clear to those skilled in the art that a logic low on the "IN" terminal will be translated to a logic low on the "OUT" terminal; the level of the output "low" tracks the voltage on the "SENSE" terminal.

As has been discussed above, in the dual channel pace delivery case (FIG. 4), a level shifter LS for transistor M2 is necessary to keep transistor M2 off when a pace pulse is generated in the other pacing channel. In the single channel case (FIG. 5), the level shifter LS associated with transistor M2 is not strictly necessary, but does help to isolate the output node "A"/"V"OUT when capacitor C1 is discharged.

FIG. 8 provides a timing diagram illustrating the switch phasing outlined above. Note the "A" pace pulse generation section. All switching is shown to be "break before make" to prevent a loss of capacitor charge due to switching transients. The broken lines associated with control lines CH2N, B and H illustrate the differences in switching if single capacitor pace pulse generation is required. In this case, only capacitor C1 is involved and the output pulse amplitude is $-V1$.

The voltage across capacitors C1 and C2 is labelled dVC1"A" and dVC2"A" in FIG. 8. The initial voltage on both capacitors is V1. During a pace pulse delivery, this voltage decays to a final value of V2. If it is assumed that the cardiac loading is purely resistive, then this decay will be exponential and easily calculated by considering the source capacitance of capacitors C1, C2 and C3 in series, the pace pulse width and the resistive loading.

This also allows for a measurement of the impedance of the high voltage defibrillating leads. Pseudo-unipolar pacing can take place using the high voltage leads DEFIB1/DEFIB2 as the ground return. The total lead impedance can then be estimated by measuring the initial and final values of voltage on the pacing capacitors. This is illustrated in FIGS. 16A and 16B which show pseudo-unipolar pacing with respect to one of the HV leads DEFIB1/DEFIB2. The size of the difference between the initial and final pace pulse voltages, shown as dVp, is indicative of the resistive loading on the pacing capacitors. This difference can either be measured by an on-board analog-to-digital converter or through a surface electrogram as disclosed in U.S. Pat. No. 4,337,776, which is hereby incorporated by reference.

In the particular embodiment disclosed herein, the "A"/"V" controller circuit (38, 40) can configure the pace pulse delivery switches such that capacitors C1 and C2 can be discharged after a pace pulse delivery. This allows for a clean transition to a lower pace delivery voltage between successive pulses. This action is illustrated in FIG. 8.

Referring back to FIGS. 4 and 5, the capacitor charging and sensing circuitry comprises p-channel transistors M12 and M13 and two CMOS transmission gates M11/M8 and M9/M10. Operation is as follows: In the two capacitor mode, i.e. when both capacitors C1 and C2 are to be charged, both transmission gates M11/M8 and M9/M10 are on at all times except during a pace pulse delivery. Therefore, the positive plates of capacitors C1 and C2 are tied together. As shown in FIG. 4, the center point of the transmission gates M11/M8, M9/M10 is used as the sense node Csense for the charge regulation circuit (34, 36). Based on a comparison of the DAC voltage and the sensed voltage Csense, the charge regulation circuit (34, 36) signals the controller circuit (38, 40) whether charging is appropriate or not. Assuming charging is required, the controller (38, 40) initiates capacitor charging by putting a logic low on lines CH1N and CH2N. In this embodiment, this occurs after a pace delivery and a possible discharge cycle are completed. The capacitors C1 and C2 are charged until the charge regulation circuit (34, 36) indicates, by changing state, that the programmed voltage has been reached. Lines CH1N and CH2N then return high, terminating charging. It is notable that any mismatch in the charging rates of capacitors C1 and C2 is compensated by the fact that they are resistively tied together through the sensing transmission gates M11/M8 and M9/M10. The impedance of these gates should be relatively low; in the described embodiment, the design value is in the 50 ohm range.

The FIG. 8 waveforms illustrate the above charging sequence. As has been noted above, single capacitor operation is illustrated by the broken lines on the switch phasing.

As stated above, it is useful to have the ability to pace at relatively high rates (50 per sec) so as to induce ventricular fibrillation. As can be seen from FIGS. 4 and 5, the maximum rate at which the pacing capacitors C1 and C2 can be recharged is effectively determined by the impedance of devices M12 and M13. Thus, with suitable device sizing, high rate pacing is possible. It should further be noted that, in implantable defibrillators, the battery internal impedance must be very low (in the 1 ohm range); therefore, it will not significantly limit the charging rates of the pacing capacitors C1 and C2.

As stated above, the coupling capacitor C3 is charged somewhat during each pace pulse delivery cycle. Transistor M1 is configured to discharge the negative plate of capacitor C3 after each pulse. The impedance of switch M1 is substantially higher than that of switches M2 through M6. A typical value is 100 ohms.

FIG. 8 shows the action of switch M1 on the output node of the pace pulse delivery circuit (30, 32). The length of time that switch M1 is on is designed so that capacitor C3 is fully discharged. As illustrated, a PACE"V" pulse occurs before switch M1 turns off. The controller circuit logic (38, 40) is designed to inhibit switch M1 when the other pace delivery channel is active. Otherwise, the other channel's pulse (PACEOUT"V" in FIG. 8) would be loaded by switch M1.

Figure 7:
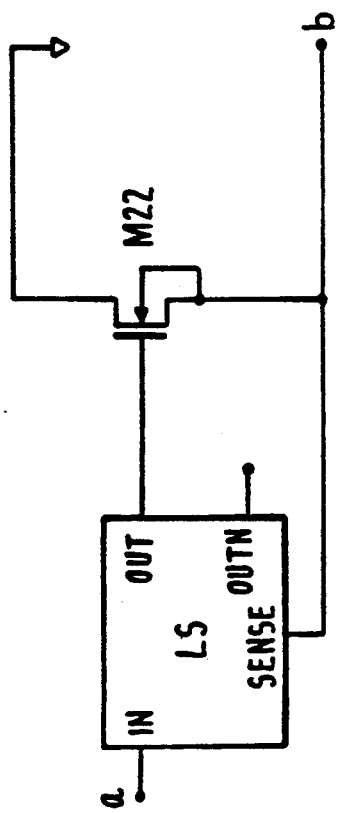
FIG. 7 is a schematic diagram illustrating an embodiment of one of the channels of the ground switching circuitry of the FIG. 2 system.

FIG. 7 shows one channel of the ground switching circuit 22 which, depending upon the configuration of circuit 22, allows each pace channel to deliver pulses in a bipolar or pseudo-unipolar fashion. Transistor M22, which is a low impedance device, connects the output node "b" to ground or allows it to float when node "a" is high or low, respectively. The ground switching circuit 22 thus allows each of the pacing ground return lines (14b, 16b) or high voltage terminals (10, 12) to be shorted to ground or to float. Transistor M22 is configured to accommodate negative voltages on its source-/bulk node and the level shifter LS is arranged such that device M22 can remain off when this node swings negative.

Referring back to FIG. 2, high voltage protection of the pace pulse output and ground switch circuits 22 is accomplished by high voltage MOSFETS Q1-Q6. The gates of these devices are driven by a PROTECTN control signal. The PROTECTN signal is normally high, ensuring that devices Q1-Q6 are on. The impedance of devices Q1-Q6 with a nominal 5 V gate drive should be in the 5 ohm range to ensure that it does not dominate the pace pulse source impedance. When high voltage protection is required, the PROTECTN control signal is switched low thus isolating the pacemaker circuitry 20 and ground switch circuitry 22 from the high voltage pulse which appears across the PACEOUT"A"/"V", ground return and HV delivery terminals. Note that the bulk connection of devices Q1-Q6 allows for protection from a positive going high voltage pulse only.

Figure 9:
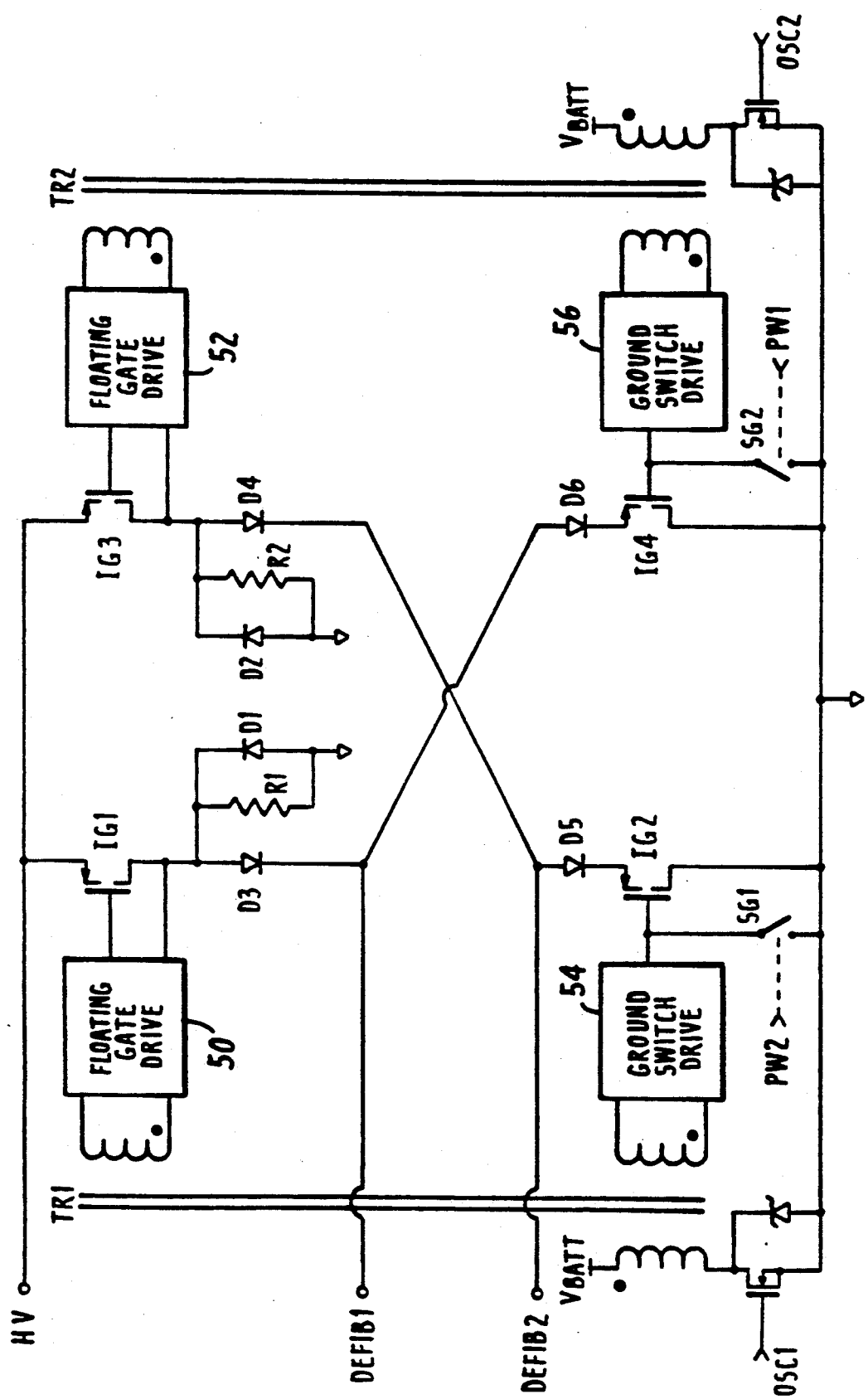
FIG. 9 is a schematic diagram illustrating a conceptual minimum configuration embodiment of HV delivery circuitry that can be utilized in the FIG. 2 system.

FIG. 9 shows a minimum configuration version of HV delivery circuitry 26. The FIG. 9 circuit basically consists of four high voltage, high current switches, shown as IGFETS IG1-IG4, configured in an "H" pattern with appropriate drive circuitry (50, 52, 54, 56, respectively) such that defibrillator output terminals DEFIB1 and DEFIB2 can be connected either to the high voltage source HV or to ground. Diode resistor pairs R1,D3 and R2,D4 protect the patient from current leakage through switches IG1 and IG3, respectively. Similarly, diodes D5 and D6 protect the patient from leakage through switches IG2 and IG4, respectively. Diodes D1 and D2 protect the circuitry from the effects of driving inductive loads.

Transformers TR1 and TR2 couple power from their respective primary windings to the floating gate drive circuits 50, 52 and the ground switch drive circuits 54, 56. Each ground switch drive circuit 54, 56 also has a corresponding switch SG1, SG2, respectively, associated with it which grounds the gate of the corresponding IGFET IG2, IG4, respectively, during alternate phase delivery to protect against inappropriate turn on due to Miller effect coupling of the drain voltage to the gate.

Figure 10:
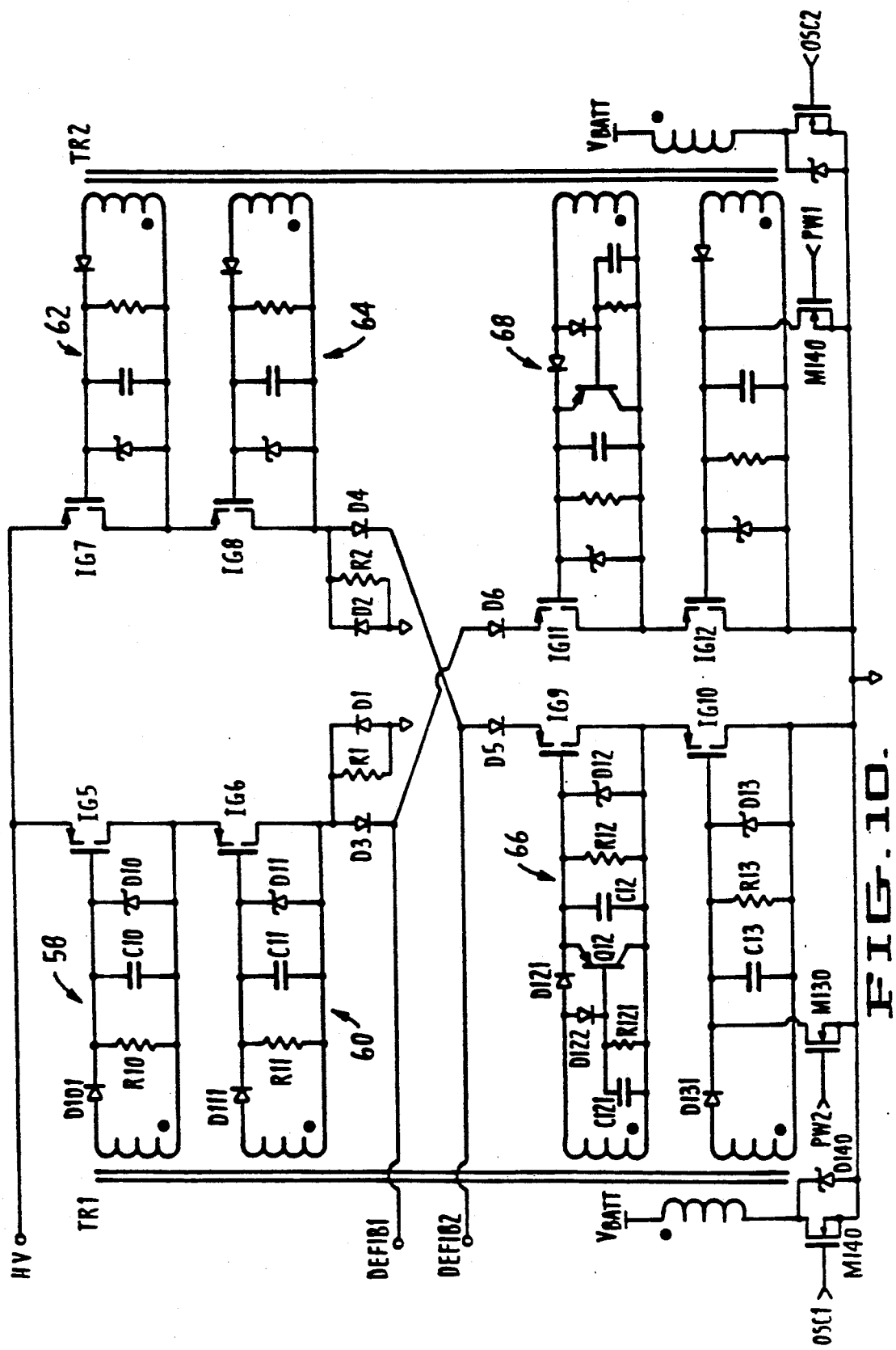
FIG. 10 is a schematic diagram illustrating a practical embodiment of the FIG. 9 HV delivery circuitry.

FIG. 10 shows a practical implementation of the HV delivery circuit of FIG. 9 where more than one high voltage switch (IGFET) is required in series to stand-off the high voltage HV. In the FIG. 10 embodiment, two floating gate switch drive circuits 58,60 and 62,64 are required to drive switches IG5,IG6 and IG7,IG8, respectively. On the ground switch side, IGFETS IG9 and IG11 are driven by slightly different floating gate drive stages 66 and 68, respectively, which include a passive scheme for protection against Miller capacitance coupled gate spikes.

Figure 11:
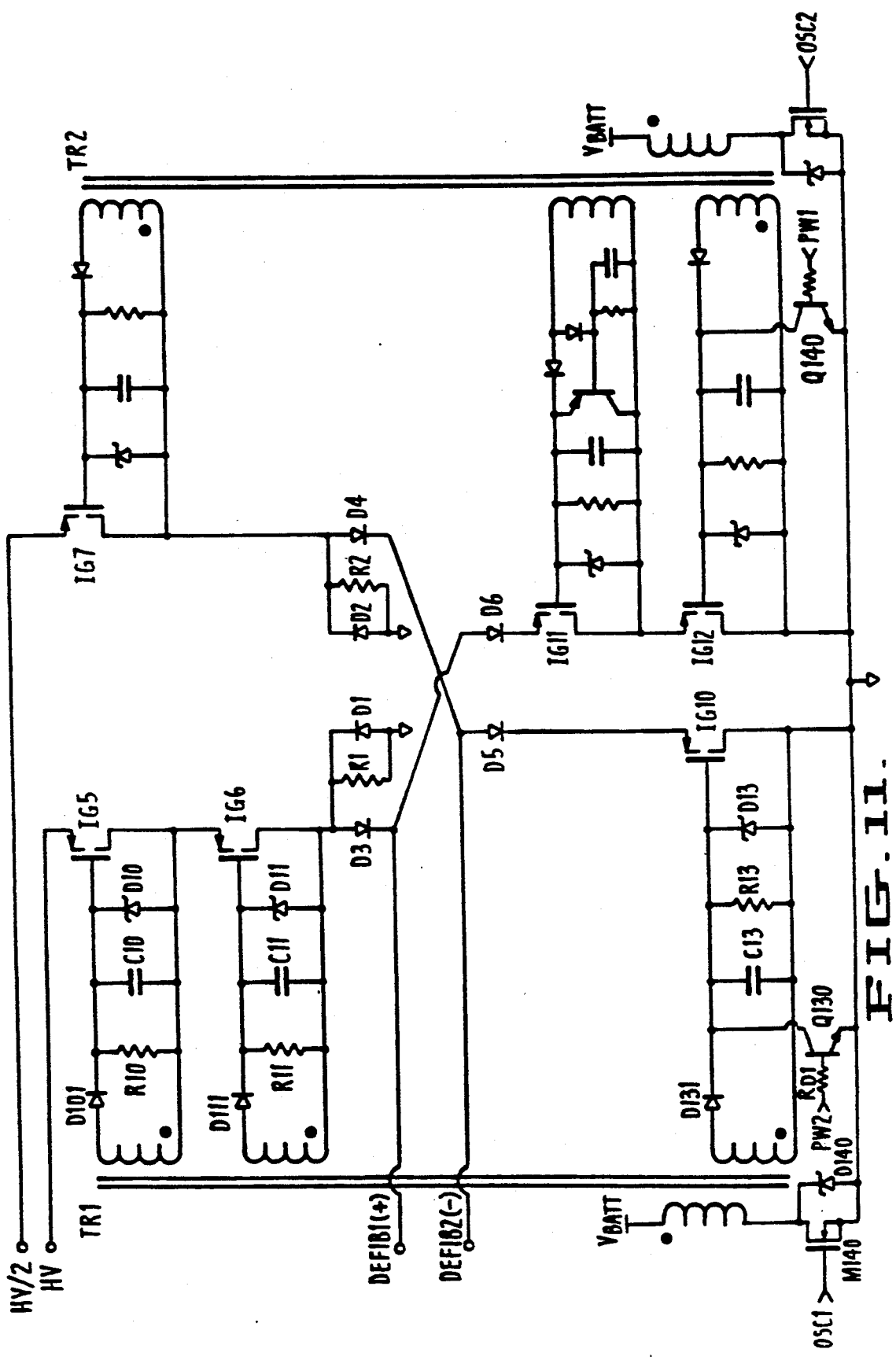
FIG. 11 is a schematic diagram illustrating a reduced component embodiment of the FIG. 10 HV delivery circuitry.

FIG. 11 shows a reduced component version of the FIG. 10 embodiment which allows for biphasic waveform generation, but limits the second phase to a maximum of half the capacitor stack voltage, i.e. HV/2.

Figure 12:
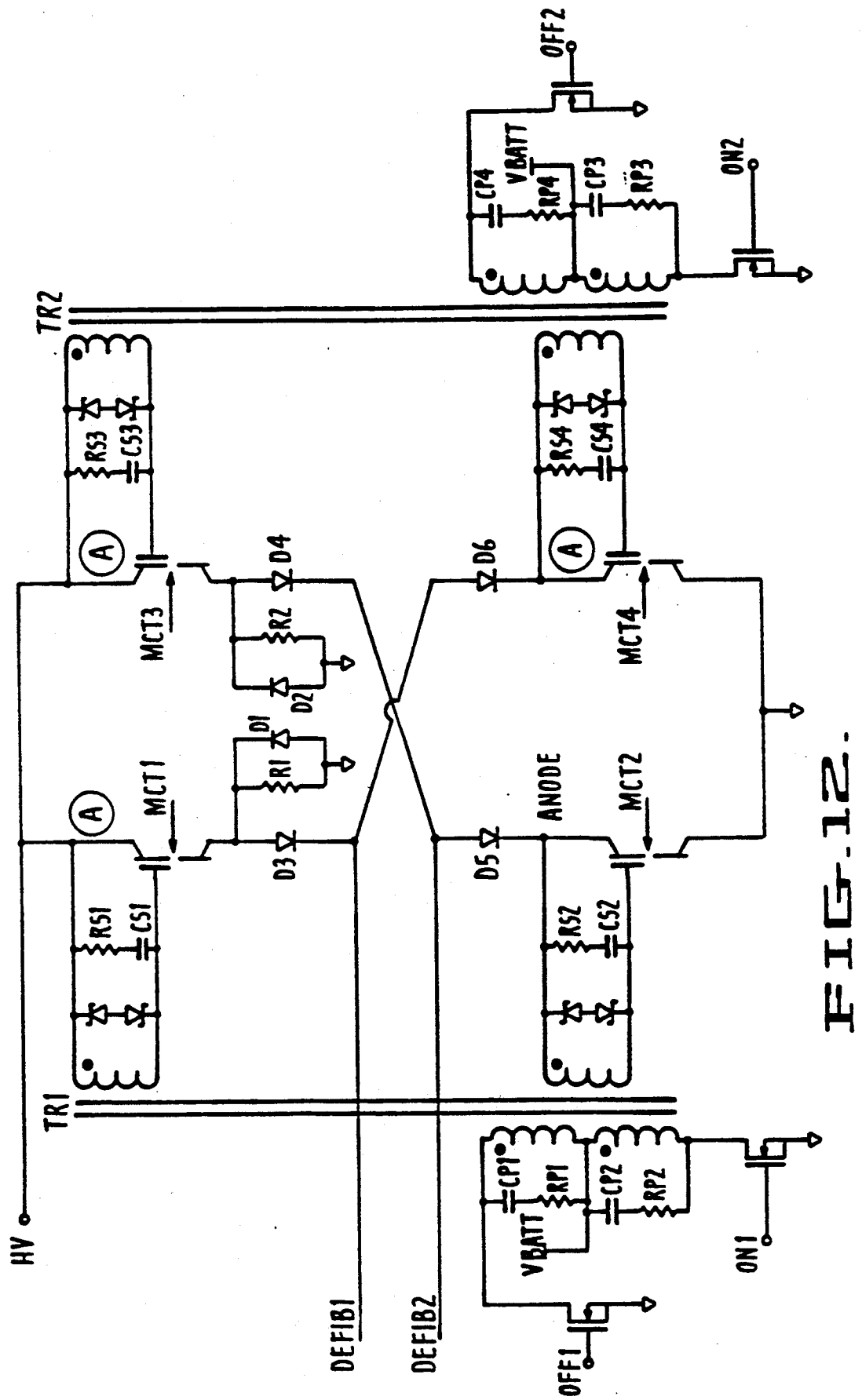
FIG. 12 is a schematic diagram illustrating an embodiment of the FIG. 9 delivery circuitry which utilizes MOS controlled thyristors as high voltage switches rather than IGFETS.
Figure 13:
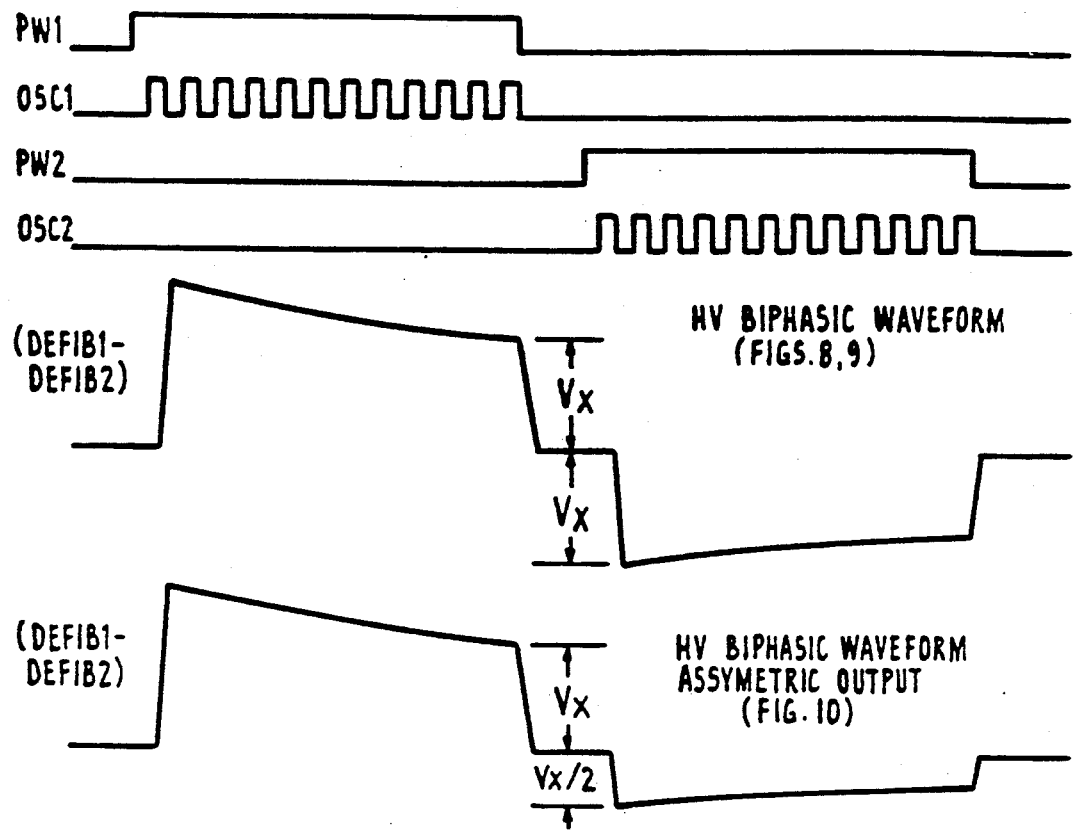
FIG. 13 is a timing diagram illustrating typical delivery waveforms associated with the FIGS. 9-11 HV delivery circuitry.

FIG. 12 shows an embodiment of the HV delivery circuit 26 which utilizes MOS controlled thyristors (MCT) as the high voltage switches rather than the IGFETS shown in the FIG. 9 embodiment. A MCT is a type of silicon controlled rectifier (SCR) which can be turned on and off by applying pulses to a single gate input; a conventional SCR can only be turned off by shunting current across it. Also, a MCT can carry higher current than an IGFET. See Goodenough, "MOS-Controlled Thyristor Turns Off 1MW in 2 uS", Electronic Design, Nov. 10, 1988, pp. 57-60.

In the MCT-based biphasic delivery circuit shown in FIG. 12, The primary coils of transformers TR1 and TR2 are snubbed by resistor/capacitor combinations RP1/CP1, RP2/CP2 and RP3/CP3, RP4/CP4, respectively, to prevent ringing. The secondary driver coils are snubbed by corresponding resistor/capacitor combinations RS1/CS1, RS2/CS2, RS3/CS3 and RS4/CS4, also to prevent ringing. With the use of MCT devices as shown, Miller effect protection becomes unnecessary.

Referring back to FIG. 9, delivery of the first phase of a biphasic high voltage pulse to the patient entails switching IGFETS IG1 and IG2 "on" with IGFETS IG3 and IG4 "off". This connects the DEFIB1 and DEFIB2 terminals to HV and ground, respectively. During the pulse delivery, the high voltage capacitor(s) are discharged somewhat. Reversing the order of the IGFETs (i.e IG1,IG2 off; IG3,IG4 on) delivers a pulse of opposite polarity to the patient. The size of this pulse is determined by the residual charge on the capacitor(s).

The energy to switch the IGFETs on is magnetically coupled through transformers TR1 and TR2. Switches IG1 and IG3 require floating gate drives (50, 52) since their source terminals track the high voltage pulse. As stated above, switches IG2 and IG4 are driven by ground switch drive circuits (54, 56). The configuration of these drive circuits will be discussed in greater detail below.

A number of significant features with regard to patient leakage and inductive ringing protection should be noted. First, as stated above, resistor/diode pairs R1,D3 and R2,D4 provide protection against leakage from HV through switches IG1 and IG3, respectively. Small leakage currents I1 are shunted to ground through resistor R1 or R2. As long as the product of I1 and R1 or R2 is less than the Vbe(on) of diodes D3 or D4, the patient will see negligible current from the HV source. Second, diodes D5 and D6 isolate the patient from leakage due to switches IG2 or IG4 during pacing. Third, diodes D1 and D2 act as snubber diodes to protect against inductive ringing below ground on the DEFIB1 and DEFIB2 terminals. Fourth, switches SG1 and SG2 (shown for generality as relays) ensure that IG2 and IG4 cannot turn on inappropriately during HV delivery. Failure to provide this protection could allow the HV pulse to be Miller capacitor coupled from drain to gate such that the device would switch on. This would short the HV to ground through essentially no load, destroying the device.

As stated above, FIG. 10 shows a practical embodiment of the circuit concept illustrated in FIG. 9. In this case, the HV to be switched is assumed to be in excess of the voltage that the IGFETs can stand off. This is quite realistic since presently available IGFETS or MOSFETS tend to be limited to 600 V at reasonable current levels (typical defibrillation voltages range up to 800 V). Hence, eight devices are required. Referring to FIGS. 10 and 12, the primary side of MOSFET M140 is driven by OSC1, a square wave. During OSC1 high time, current is built up in the primary coil of transformer TR1. When OSC1 switches low, the drain of device M140 flies back, coupling energy through the magnetics to the secondary coils. Current is supplied through diodes D101, D111, D121, D131 to the gates of devices IG5, IG6, IG9, IG10, respectively, turning them on and delivering the first half of the biphasic pulse. On each cycle of OSC1, energy is coupled across to counteract the effect of the passive pull down resistors R10 through R13. Zener diodes D10 through D13 protect the IGFET gates from overvoltage. Capacitors C10 through C13 reduce the voltage ripple seen at the IGFET gates.

At the termination of the PW1 pulse, OSC1 returns low and passive pull downs R10-R13 switch off the IGFETs. This terminates the first phase of the biphasic waveform.

Generation of the second phase of the biphasic waveform is achieved by simply activating the second transformer via OSC2. During this time, it should be noted, device MI30 is on, thus grounding the gate of switch IG10 and ensuring that it remains off regardless of Miller capacitance coupling of the HV pulse from gate to drain. The floating gate drive of switch IG9 is protected by the arrangement of circuit elements Q12, R121, C121, D122. It will be clear to those skilled in the art that this arrangement is equivalent to a capacitor of value C121 * Beta of Q12 connected in parallel with C12. This capacitance is only apparent transiently when device Q12 is turned on by positive going (Miller capacitance) spikes on its emitter. Hence, the turn on time of switch IG9 is unaffected.

As stated above, FIG. 11 shows a circuit configuration which requires fewer components than the circuit illustrated in FIG. 10. In this case, switches IG7 and IG10 only have to stand off HV/2 which is taken from the centertap of the high voltage capacitor stack, as shown in FIG. 2. This means that the second phase of the high voltage pulse can only reach a maximum value of HV/2, assuming no load. Otherwise operation of this circuit is identical to that shown in FIG. 10 Note that the pull down devices M130 and M140 can be replaced by bipolar devices Q130 and Q140 as shown.

One of the problems associated with the IGFET-based HV delivery circuits discussed earlier is that, as the battery voltage Vbatt drops under load, or through life, the maximum energy per cycle which can be coupled to the transformer secondaries drops in proportion to Vbatt squared. In fact, the power developed in the primary is given by $$P = (Vbatt)^2 * T/2L$$

where: T is the periodic time of the of the cycle (assuming square wave) and L is the inductance of the primary.

Hence, the transformer has to be substantially overdesigned so as to be able to couple sufficient energy to the secondaries at all battery voltages.

Figure 15:
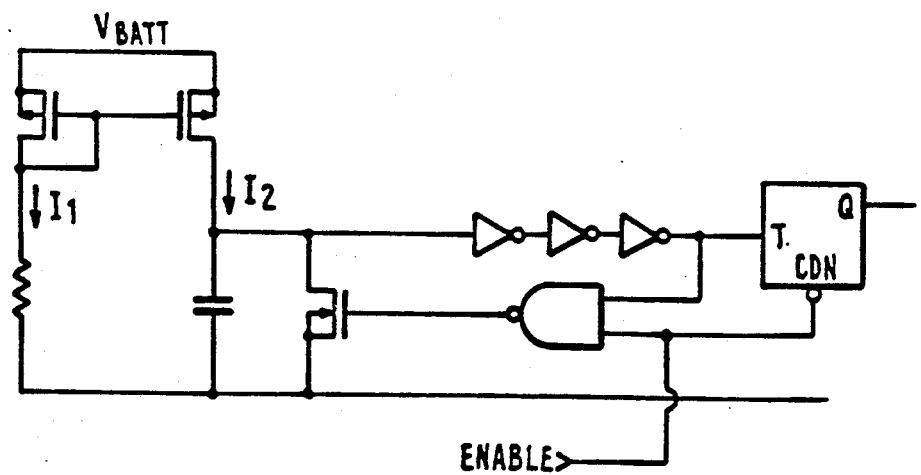
FIG. 15 is a schematic diagram illustrating an embodiment of HV delivery oscillator circuitry that can be utilized in the FIG. 2 system.
Figure 14:
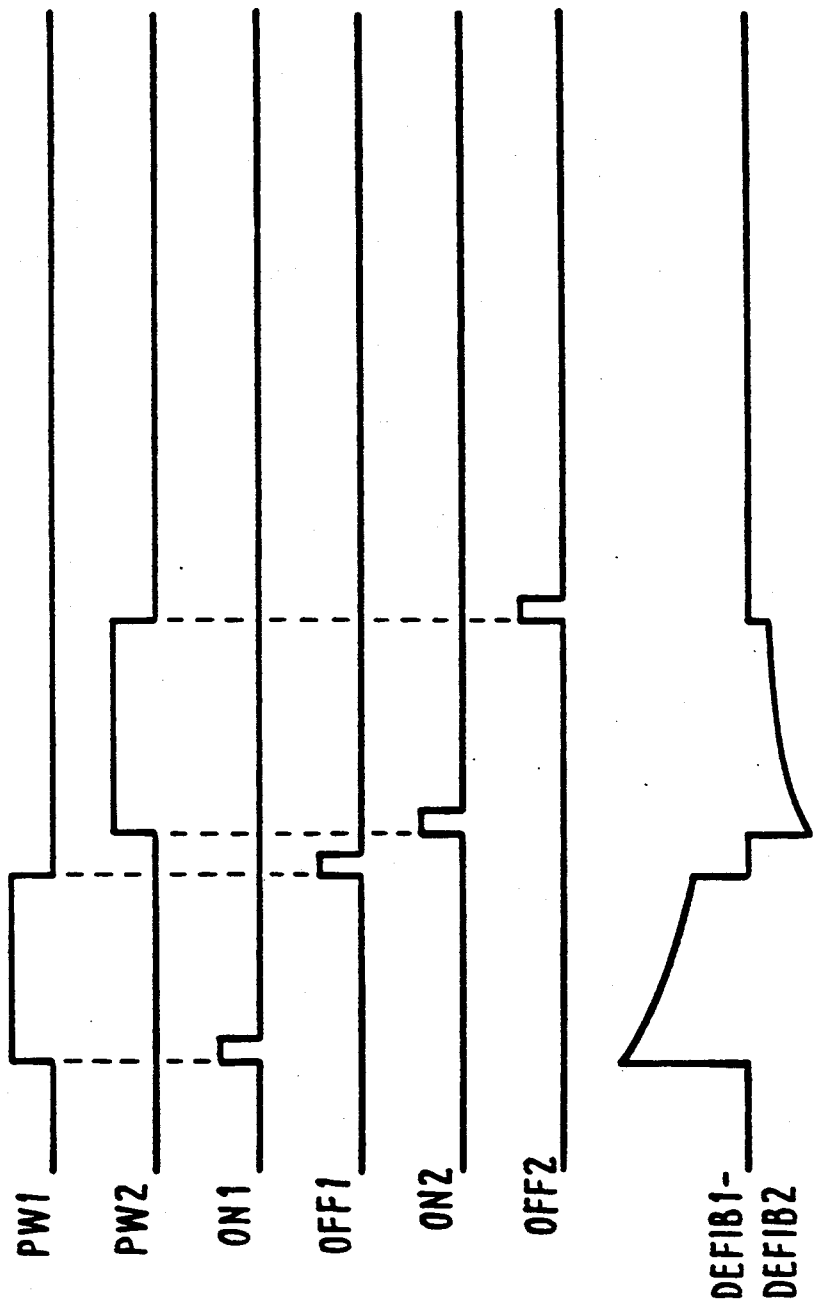
FIG. 14 is a timing diagram illustrating typical waveforms associated with the FIG. 12 delivery circuit.

The type of oscillator circuit shown in FIG. 15 helps to alleviate this problem somewhat.

FIG. 15 shows an embodiment of a HV delivery oscillator circuit which is used to generate a 50% duty cycle output which has a periodic time which varies approximately linearly with battery voltage. This relationship is exploited to keep the peak magnetic fields in the HV delivery circuit transformers approximately constant with battery voltage. This allows for a greatly optimized transformer design.

It can be shown that for this oscillator that its periodic time T has the following relationship to battery voltage:

$$T = K/(Vbatt - Vtp)$$

where Vtp is the threshold voltage of the p-channel transistors in FIG. 15.

Substituting this value into the equation for P provided above gives $$P = KI^*(Vbatt)^2 / Vbatt - Vtp$$

Assuming Vbatt much greater than Vtp, then $$P = KI^* Vbatt$$

Hence, the power level would drop only linearly with battery voltage. Furthermore the maximum current present in the primary can be shown to be:

$$Imax = K2/(L^*(1 - Vtp/Vbatt))$$

Hence, when Vbatt is significantly larger than Vtp, the maximum current, and thus the maximum magnetic field, will increase slowly with battery voltage. This permits a much more optimized transformer (size) than would otherwise be possible.

It is intended that the term "biphasic" as used in this document cover the case where the pulsewidth of the second defibrillation phase is zero, i.e. when the high voltage delivery is essentially monophasic.

It should also be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. In an implantable medical device utilizable for delivering a biphasic defibrillation waveform to the heart and including first and second defibrillation electrodes adapted to be connected to the heart, charging circuitry for generating a defibrillation signal, delivery circuitry responsive to control signals for selectively providing the defibrillation signal to the first and second defibrillation electrodes and control means for generating the control signals, the delivery circuitry comprising:
   (a) first switching means disposed between the charging circuitry and the first defibrillation electrode and responsive to a first floating gate drive signal for providing the defibrillation signal to the first defibrillation electrode;
   (b) second switching means disposed between the second defibrillation electrode and ground and responsive to a first ground switch drive signal for connecting the second defibrillation electrode to ground;
   (c) third switching means disposed between the charging circuitry and the second defibrillation electrode and responsive to a second floating gate drive signal for providing the defibrillation signal to the second defibrillation electrode;
   (d) fourth switching means disposed between the first defibrillation electrode and ground and responsive to a second ground switch drive signal for connecting the first defibrillation electrode to ground;
   (e) means responsive to a first control signal for simultaneously generating the first floating gate drive signal and the first ground switch drive signal; and
   (f) means responsive to a second control signal for simultaneously generating the second floating gate drive signal and the second ground switch drive signal
   wherein each of the first and third switching means further includes means for preventing current leakage through the switching means to the corresponding defibrillation electrode.

2. An implantable medical device as in claim 1 wherein the means for preventing current leakage comprises a resistor connected between the switching means and ground and a diode connected between the switching means and its corresponding defibrillation electrode.

3. In an implantable medical device utilizable for delivering a biphasic defibrillation waveform to the heart and including first and second defibrillation electrodes adapted to be connected to the heart, charging circuitry for generating a defibrillation signal, delivery circuitry responsive to control signals for selectively providing the defibrillation signal to the first and second defibrillation electrodes and control means for generating the control signals, the delivery circuitry comprising:
   (a) first switching means disposed between the charging circuitry and the first defibrillation electrode and responsive to a first floating gate drive signal for providing the defibrillation signal to the first defibrillation electrode;
   (b) second switching means disposed between the second defibrillation electrode and ground and responsive to a first ground switch drive signal for connecting the second defibrillation electrode to ground;
   (c) third switching means disposed between the charging circuitry and the second defibrillation electrode and responsive to a second floating gate drive signal for providing the defibrillation signal to the second defibrillation electrode;
   (d) fourth switching means disposed between the first defibrillation electrode and ground and responsive to a second ground switch drive signal for connecting the first defibrillation electrode to ground;
   (e) means responsive to a first control signal for simultaneously generating the first floating gate drive signal and the first ground switch drive signal; and
   (f) means responsive to a second control signal for simultaneously generating the second floating gate drive signal and the second ground switch drive signal
   wherein each of the first and third switching means further includes a snubber diode connected between the switching means and ground for protecting against inductive ringing below ground on the corresponding defibrillation electrode.

4. In an implantable medical device utilizable for delivering a biphasic defibrillation waveform to the heart and including first and second defibrillation electrodes adapted to be connected to the heart, charging circuitry for generating a defibrillation signal, delivery circuitry responsive to control signals for selectively providing the defibrillation signal to the first and second defibrillation electrodes and control means for generating the control signals, the delivery circuitry comprising:
   (a) first switching means disposed between the charging circuitry and the first defibrillation electrode and responsive to a first floating gate drive signal for providing the defibrillation signal to the first defibrillation electrode;

(b) second switching means disposed between the second defibrillation electrode and ground and responsive to a first ground switch drive signal for connecting the second defibrillation electrode to ground;

(c) third switching means disposed between the charging circuitry and the second defibrillation electrode and responsive to a second floating gate drive signal for providing the defibrillation signal to the second defibrillation electrode;

(d) fourth switching means disposed between the first defibrillation electrode and ground and responsive to a second ground switch drive signal for connecting the first defibrillation electrode to ground;

(e) means responsive to a first control signal for simultaneously generating the first floating gate drive signal and the first ground switch drive signal; and (f) means responsive to a second control signal for simultaneously generating the second floating gate drive signal and the second ground switch drive signal wherein each of the second and fourth switching means further includes means for protecting against Miller capacitance voltage spikes.

5. In an implantable medical device as in claim 4 wherein the means for protecting against Miller capacitance voltage spikes comprises a switch connected between the corresponding ground switch drive signal and ground.

6. In an implantable medical device utilizable for delivering a biphasic defibrillation waveform to the heart and including first and second defibrillation electrodes adapted to be connected to the heart, charging circuitry for generating a defibrillation signal, delivery circuitry responsive to control signals for selectively providing the defibrillation signal to the first and second defibrillation electrodes and control means for generating the control signals, the delivery circuitry comprising:

(a) first switching means disposed between the charging circuitry and the first defibrillation electrode and responsive to a first floating gate drive signal for providing the defibrillation signal to the first defibrillation electrode;

(b) second switching means disposed between the second defibrillation electrode and ground and responsive to a first ground switch drive signal for connecting the second defibrillation electrode to ground;

(c) third switching means disposed between the charging circuitry and the second defibrillation electrode and responsive to a second floating gate drive signal for providing the defibrillation signal to the second defibrillation electrode;

(d) fourth switching means disposed between the first defibrillation electrode and ground and responsive to a second ground switch drive signal for connecting the first defibrillation electrode to ground;

(e) means responsive to a first control signal for simultaneously generating the first floating gate drive signal and the first ground switch drive signal; and (f) means responsive to a second control signal for simultaneously generating the second floating gate drive signal and the second ground switch drive signal wherein each of the second and fourth switching means further includes a diode connected between the switching means and the corresponding defibrillation electrode.

7. In an implantable medical device for delivering a defibrillation waveform to a heart, the medical device including first and second defibrillation electrodes adapted to be attached to the heart, first and second defibrillation leads connected to the first and second defibrillation electrodes, respectively, means for generating a defibrillation signal, delivery circuitry responsive to first and second control signals for selectively providing the defibrillation signal to the first and second defibrillation leads such that the delivery circuitry provides a defibrillation waveform to the heart, the delivery circuitry comprising:

(a) first switching means comprising first and second series-connected IGFET devices, the drain of the first IGFET device connected to receive the defibrillation signal, the source of the second IGFET device connected to the first defibrillation lead, the gate of each of the first and second IGFET devices connected to receive a first floating gate drive signal;

(b) second switching means comprising third and fourth series-connected IGFET devices, the drain of the third IGFET device connected to the second defibrillation lead, the source of the fourth IGFET device connected to ground, the gate of each of the first and second IGFET devices connected to receive a first ground switch drive signal;

(c) third switching means comprising fifth and sixth series-connected IGFET devices, the drain of the fifth IGFET device connected to receive the defibrillation signal, the source of the sixth IGFET device connected to the second defibrillation lead, and the gate of each of the fifth and sixth IGFET devices connected to receive a second floating gate drive signal;

(d) fourth switching means comprising seventh and eighth series-connected IGFET devices, the drain of the seventh IGFET device connected to the first defibrillation lead, the source of the eighth IGFET device connected to ground, the gate of each of the seventh and eighth IGFET devices connected to receive a second ground switch drive signal;

(e) means for generating first and second floating gate drive signals, responsive to the first and second control signals, respectively, for coupling power in an isolated fashion to the first and second floating gate drives;

(f) means for generating first and second ground switch drive signals, responsive to the first and second control signals respectively, for coupling power in an isolated fashion to the first and second ground switch drives;

(g) means responsive to the first control signal for generation of the first floating gate drive signal and the first ground switch drive signal in an isolated fashion such that the first, second, third and fourth IGFET devices are turned on; and (h) means responsive to the second control signal for generating the second floating gate drive signal and the second ground switch drive signal in an isolated fashion such that the fifth, sixth, seventh and eighth IGFET devices are turned on.

8. In an implantable medical device for delivering a defibrillation waveform to a heart, the medical device including first and second defibrillation electrodes adapted to be attached to the heart, first and second defibrillation leads connected to the first and second defibrillation electrodes, respectively, means for generating a defibrillation signal, delivery circuitry responsive to first and second control signals for selectively providing the defibrillation signal to the first and second defibrillation leads such that the delivery circuitry provides a defibrillation waveform to the heart, the delivery circuitry comprising:

(a) first switching means comprising first and second series-connected IGFET devices, the drain of the first IGFET device connected to receive the defibrillation signal, the source of the second IGFET device connected to the first defibrillation lead, the gate of each of the first and second IGFET devices connected to receive a first floating gate drive signal;

(b) second switching means comprising a third IGFET device having its drain connected to the second defibrillation lead, its source connected to ground, and its gate connected to receive a first ground switch drive signal;

(c) third switching means comprising a fourth IGFET device having its drain connected to receive half the defibrillation signal, its source connected to the second defibrillation lead, and its gate connected to receive a second floating gate drive signal;

(d) fourth switching means comprising fifth and sixth series-connected IGFET devices, the drain of the fifth IGFET device connected to the first defibrillation lead, the source of the sixth IGFET device connected to ground, the gate of each of the fifth and sixth IGFET devices connected to receive a second ground switch drive signal;

(e) means for generating first and second floating gate drive signals, responsive to the first and second control signals, respectively, for coupling power in an isolated fashion to the first and second floating gate drives;

(f) means for generating first and second ground switch drive signals, responsive to the first and second control signals, respectively, for coupling power in an isolated fashion to the first and second ground switch drives;

(g) means responsive to the first control signal for generating the first floating gate drive signal and the first ground switch drive signal in an isolated fashion such that the first, second, and third IGFET devices are turned on; and (h) means responsive to the second control signal for generation of the second floating gate drive signal and the second ground switch drive signal in an isolated fashion such that the fourth, fifth, and sixth IGFET devices are turned on.

9. An implantable medical device as in claim 7 or 8 wherein each of the first and third switching means further includes means for preventing current leakage through the switching means to the corresponding defibrillation lead.

10. An implantable medical device as in claim 7 or 8 wherein each of the first and third switching means includes a resistor connected between the switching means and ground and a diode connected between the switching means and the corresponding defibrillation lead for preventing current leakage through the switching means into the defibrillation lead.

11. An implantable medical device as in claim 7 or 8 wherein each of the first and third switching means further includes a snubber diode connected between the switching means and ground for protecting against inductive ringing below ground on the corresponding defibrillation lead.

12. An implantable medical device as in claim 7 or 8 wherein each of the second and fourth switching means further includes means for protecting against Miller capacitance voltage spikes.

13. An implantable medical device as in claim 7 or 8 wherein each of the second and fourth switching means further includes a switch connected between the corresponding ground switch drive signal and ground for grounding the corresponding IGFET gate during alternate phase delivery.

14. An implantable medical device as in claim 7 or 8 wherein each of the second and fourth switching means further includes a diode connected between the switching means and the corresponding defibrillation lead.

15. An implantable medical device as in claim 7 or 8 wherein the delivery circuitry further includes means for maintaining the magnetic fields in each of the first and second transformer means approximately constant with respect to battery voltage.

16. An implantable medical device that utilizes positive battery voltage to deliver negative pacing pulses to a heart, the implantable medical device comprising:

(a) a battery for providing a positive battery voltage;

(b) a first capacitor having its top plate connectable to the positive battery voltage and its bottom plate connectable to ground;

(c) a second capacitor having its top plate connectable to the positive battery voltage and its bottom plate connectable to ground;

(d) a pacing output node;

(e) means connectable between the first and second capacitors and the positive battery voltage for charging the top plates of the first and second capacitors to a preselected positive voltage;

(f) means connectable to the top plates of the first and second capacitors for sensing that the top plates of the first and second capacitors have been charged to the preselected positive voltage;

(g) means connectable between the first and second capacitors and the pacing output node and responsive to a first control signal set for shifting the bottom plate of the second capacitor to the negative of the preselected voltage and for shifting the bottom plate of the first capacitor to twice the negative of the preselected positive voltage and connecting the bottom plate of the first capacitor to the pacing output node; and (h) pacing electrode means adapted to be connected between the pacing output node and the heart for delivering twice the negative of the preselected positive voltage to the heart.

17. An implantable medical device that utilizes positive battery voltage to deliver negative pacing pulses to a heart, the implantable medical device comprising:

(a) a battery for providing a positive battery voltage;

(b) a first capacitor having its top plate connectable to the positive battery voltage and its bottom plate connectable to ground;

(c) a pacing output node;

(d) means connectable between the first capacitor and the positive battery voltage for charging the top plate of the first capacitor to a preselected positive voltage;

(e) means connectable to the top plate of the first capacitor for sensing that the top plate of the first capacitor has been charged to the preselected positive voltage;

(f) pacing electrode means adapted to be connected between the output node and the heart; and (g) means connectable between the first capacitor and the pacing output node and responsive to a first set of control signals for inverting the first capacitor such that the negative of the preselected positive voltage is connected to the pacing output node.

18. An implantable medical device that utilizes positive battery voltage to deliver negative pacing pulses to a heart, the implantable medical device comprising:

(a) a battery for providing a positive battery voltage;

(b) a first capacitor having its top plate connectable to the positive battery voltage via a first switch and its bottom plate connectable to ground via a second switch;

(c) a second capacitor having its top plate connectable to the positive battery voltage via a third switch and its bottom plate connectable to ground via a fourth switch;

(d) a pacing output node;

(e) a fifth switch connected between the bottom plate of the first capacitor and the pacing output node;

(f) a sixth switch connected between the top plate of the second capacitor and ground;

(g) a seventh switch connected between the top plate of the first capacitor and the bottom plate of the second capacitor;

(h) means for closing the first and third switches while the second and fourth switches are also closed and while the fifth through seventh switches are open such that the top plates of the first and second capacitors are charged to a preselected positive voltage;

(i) charge regulation means connected to the top plate of the first capacitor and the top plate of the second capacitor for sensing that the top plates of the first and second capacitors have been charged to the preselected positive voltage and which then opens the first and third switches;

(j) means responsive to a first control signal set for opening the second and fourth switches and then closing the fifth, sixth and seventh switches such that the bottom plate of the second capacitor is shifted to a first negative voltage and the bottom plate of the first capacitor is shifted to a second negative voltage and the pacing output node is connected to the bottom plate of the first capacitor;

(k) means responsive to the trailing edge of the first control signal such that fifth, sixth and seventh switches are turned off and then the second and fourth switches turned on; and (l) pacing electrode means adapted to be connected between the output node and the heart for delivering the second negative voltage to the heart.

19. An implantable medical device that utilizes positive battery voltage to deliver negative pacing pulses to a heart, the implantable medical device comprising:

(a) a battery for providing a positive battery voltage;

(b) a first capacitor having its top plate connectable to the positive battery voltage via a first switch and its bottom plate connectable to ground via a second switch;

(c) a second capacitor having its top plate connectable to the positive battery voltage via a third switch and its bottom plate connectable to ground via a fourth switch;

(d) a pacing output node;

(e) a fifth switch connected between the bottom plate of the first capacitor and the pacing output node;

(f) a sixth switch connected between the top plate of the second capacitor and ground;

(g) a seventh switch connected between the top plate of the first capacitor and the bottom plate of the second capacitor;

(h) means for closing the first switch while the second switch is also closed and while the third through seventh switches are open such that the top plate of the first capacitor is charged to a positive preselected voltage;

(i) charge regulation means connected to the top plate of the first capacitor for sensing that the top plate of the first capacitor has been charged to the positive preselected voltage and which then opens the first switch;

(j) means responsive to a first control signal set for opening the second switch and then closing the fourth, fifth and seventh switches such that the bottom plate of the first capacitor is shifted to the negative of the preselected voltage and connected to the pacing output node;

(k) means responsive to the trailing edge of the first control signal such that the fourth, fifth and seventh switches are turned off and then the second switch turned on; and (l) pacing electrode means adapted to be connected between the pacing output node and the heart for delivering the negative voltage to the heart.

20. An implantable medical device as in claim 16, 17, 18 or 19 wherein the fifth switch includes means for blocking a negative voltage such that a negative voltage applied to the pacing output node has no current path to any of the internal circuit nodes of the device.

21. An implantable medical device as in claim 16, 17, 18 or 19 and further including means for charging the first and second capacitor at a rate such that the pacing pulses can be delivered to the heart at a rate greater than about 50 pulses per second.

22. An implantable medical device for delivering pacing signals to a heart, the device comprising:

(a) a battery for providing a positive battery voltage;

(b) pacemaker circuitry means responsive to the positive battery voltage for generating negative pacing signals;

(c) pacing electrode means adapted to be connected to the heart for delivering the negative pacing signals to the heart; and (d) protection means connected between the pacemaker circuitry and the pacing electrode means for passing the negative placing signals from the pacemaker circuitry to the pacing electrode means and for selectively preventing signals from passing from the pacing electrode means to the pacemaker circuitry.

23. An implantable medical device for delivering pacing signals to a heart, the device comprising:

(a) a battery for providing a positive battery voltage;

(b) pacemaker circuitry means responsive to the positive battery voltage for generating negative pacing signals;

(c) a pair of pacing leads adapted to be connected to the heart for delivering the negative pacing signals to the heart, the pacing leads comprising an active lead and a ground return lead;

(d) defibrillation means connected to the heart for delivering a defibrillation signal to the heart; and (e) protection means connected between the pacemaker circuitry and the pacing leads for preventing the defibrillation signal from passing from the heart to the pacemaker circuitry via the pacing leads, the protection means comprising a switch connected between the pacemaker circuitry means and the active lead and responsive to a first state of a protection control signal to pass the pacing signals to the heart via the active pacing lead and responsive to a second state of the protection control signal to prevent the defibrillation signal form passing from the heart to the pacemaker circuitry via the active lead.

24. An implantable medical device for delivering pacing signals to the heart, the device comprising:

(a) pacing leads adapted to be connected to the heart for delivering the pacing signals to the heart, the pacing leads comprising an active lead and a ground return lead;

(b) defibrillation means connected to the heart for delivering a defibrillation signal to the heart;

(c) pacemaker circuitry for generating the pacing signals;

(d) ground switch circuitry for selectively shorting the ground return lead to ground; and (e) protection means comprising
  (i) a first protection switch connected between the pacemaker circuitry and the active lead for preventing the defibrillation signal from passing from the heart to the pacemaker circuitry via the active lead; and
  (ii) a second protection switch connected between the ground switch circuitry and the ground return lead for preventing the defibrillation signal from passing from the heart to the ground switch circuitry via the ground return lead.

25. An implantable medical device as in claim 24 wherein the protection means further comprises means connecting the defibrillation means to the ground switch circuitry and including switching means for preventing the defibrillation signal from passing from the defibrillation means to the ground switch circuitry.

26. An implantable medical device as in claim 25 wherein the defibrillation means includes first and second defibrillation leads connected to the heart for delivering a biphasic defibrillation waveform to the heart and the protection means further includes:

(a) a third protection switch connected between the first defibrillation lead and the ground switch circuitry; and (b) a fourth protection switch connected between the second defibrillation lead and the ground switch circuitry.

27. An implantable medical device for delivering pacing signals to a heart, the device comprising:

(a) a first pair of pacing leads adapted to be connected to a first region of the heart for delivering pacing signals to the first region and comprising a first active lead and a first return lead;

(b) a second pair of pacing leads adapted to be connected to a second region of the heart for delivering pacing signals to the second region and comprising a second active lead and a second return lead;

(c) a battery for providing a positive battery voltage;

(d) first pacing pulse generation means responsive to the positive battery voltage for generating first negative pacing signals;

(e) first pace pulse delivery means for providing the first negative pacing signals to the heart via the first active lead in response to a first control signal;

(f) second pacing pulse generation means responsive to the positive battery voltage for generating second negative pacing signals;

(g) second pace pulse delivery means for providing the second negative pacing signals to the heart via the second active lead in response to a second control signal; and (h) means for isolating the first negative pacing signals from the second negative pacing signals.

28. An implantable medical device as in claims 16, 17, 18, 19, 22, 24, or 27 and further comprising defibrillation means for delivering a defibrillation signal to the heart, the defibrillation means comprising:

(a) defibrillation electrode means adapted to be connected to the heart;

(b) charging means for generating a defibrillation signal;

(c) switching means connected between the defibrillation electrode means and the charging means and responsive to a control signal for selectively providing the defibrillation signal to the defibrillation electrode means; and (d) control means for generating the control signal, wherein the switching means includes current leakage control means or shunting leakage current from the charging means away from the defibrillation electrode means.

29. An implantable medical device as in claims 16, 17, 18, 19, 22, 24 or 27 and further comprising defibrillation means for delivering a defibrillation signal to the heart, the defibrillation means comprising:

(a) defibrillation electrode means adapted to be connected to the heart;

(b) charging means for generating a defibrillation signal;

(c) switching means connected between the defibrillation electrode means and the charging means and responsive to a control signal for selectively providing the defibrillation signal to the defibrillation electrode means;

(d) control means for generating the control signal; and (e) a snubber diode connected between the switching means and ground for protecting the defibrillation electrode means against over-voltage due to inductive ringing.

30. An implantable medical device as in claims 16, 17, 18, 19, 22 or 27 and further comprising defibrillation means for delivering a defibrillation signal to the heart, the defibrillation means comprising:

(a) defibrillation electrode means adapted to be connected to the heart;

(b) charging means for generating a defibrillation signal;

(c) electrode stage switching means connected between the charging circuitry and the defibrillation electrode means and responsive to an electrode switch drive signal for selectively providing the defibrillation signal to the defibrillation electrode means;

(d) ground stage switching means connected between the defibrillation electrode means and ground and responsive to a ground switch drive signal for selectively connecting the defibrillation means to ground;

(e) control means for generating the electrode switch drive signal and the ground switch drive signal; and (f) a protection switch connected between the ground stage switching means and ground and responsive to a voltage spike generated by the ground stage switching means for preventing connection of the defibrillation electrode means to ground in response to the voltage spike.

31. An implantable medical device for delivering signals to a heart, the device comprising:
    (a) pacing leads adapted to be connected between pacemaker circuitry and the heart for delivering the pacing signals to the heart, the pacing leads comprising an active lead and a ground return lead;
    (b) pacemaker circuitry for generating the pacing signals;
    (c) defibrillation means connected to the heart for delivering defibrillation signals to the heart, the defibrillation means comprising
        (i) means for generating the defibrillation signals;
        (ii) defibrillation electrodes adapted to be connected to the heart; and
        (iii) defibrillation leads connected between the means for generating and the electrodes for providing the defibrillation signals to the electrodes; and
    (d) ground switch circuitry connected to the defibrillation leads and the ground return lead such that any one or any combination of said leads can be selectively connected to ground, those leads not connected to ground being allowed to float, such that pacing can be bipolar with the ground return lead connected to ground, or pseudo-unipolar with either or both of the defibrillation leads being connected to ground.

32. An implantable medical device as in claim 31 and further including means for selectively connecting either of the defibrillation leads to ground with the pacing ground return lead floating such that the device provides means for assessing the impedance of the defibrillation leads when a pacing pulse is delivered.

33. An implantable medical device as in claim 32 and further comprising means for periodically checking the impedance of the defibrillation lead to determine whether a break in the defibrillation lead is detected.

34. An implantable medical device as in claim 33 and further including means for generating a warning signal indicating that a break in the defibrillation lead has been detected.

35. An implantable medical device utilizable for delivering a defibrillation signal to a heart, the implantable medical device comprising:
    (a) defibrillation electrode means adapted to be connected to the heart;
    (b) charging means for generating a defibrillation signal;
    (c) switching means connected between the defibrillation electrode means and the charging means and responsive to a control signal for selectively providing the defibrillation signal to the defibrillation electrode means; and
    (d) control means for generating the control signal, wherein the switching means includes current leakage control means for shunting leakage current from the charging means away from the defibrillation electrode means.

36. An implantable medical device utilizable for delivering a defibrillation signal to a heart, the implantable medical device comprising:
    (a) defibrillation electrode means adapted to be connected to the heart;
    (b) charging means for generating a defibrillation signal;
    (c) switching means connected between the defibrillation electrode means and the charging means and responsive to a control signal for selectively providing the defibrillation signal to the defibrillation electrode means;
    (d) control means for generating the control signal; and
    (e) a snubber diode connected between the switching means and ground for protecting the defibrillation electrode means against over-voltage due to inductive ringing.

37. An implantable medical device utilizable for delivering a defibrillation signal to a heart, the implantable medical device comprising:
    (a) defibrillation electrode means adapted to be connected to the heart;
    (b) charging means for generating a defibrillation signal;
    (c) electrode stage switching means connected between the charging circuitry and the defibrillation electrode means and responsive to an electrode switch drive signal for selectively providing the defibrillation signal to the defibrillation electrode means;
    (d) ground stage switching means connected between the defibrillation electrode means and ground and responsive to a ground switch drive signal for selectively connecting the defibrillation electrode means to ground;
    (e) control means for generating the electrode switch drive signal and the ground switch drive signal; and
    (f) a protection switch connected between the ground stage switching means and ground and responsive to a voltage spike generated by the ground stage switching means for preventing connection of the defibrillation electrode means to ground in response to the voltage spike.

* * * * *